United States Patent
Lorberbaum et al.

(10) Patent No.: US 9,463,287 B1
(45) Date of Patent: Oct. 11, 2016

(54) CONTROLLING USAGE OF REPLACEABLE TOOL ENDS

(71) Applicant: Bing Innovations, LLC, Boca Raton, FL (US)

(72) Inventors: Mark Lorberbaum, Boca Raton, FL (US); Bernardo Yagoda, Waltham, MA (US)

(73) Assignee: BING INNOVATIONS, LLC, Boca Raton, FL (US)

( * ) Notice: Subject to any disclaimer, the term of this patent is extended or adjusted under 35 U.S.C. 154(b) by 0 days.

(21) Appl. No.: 14/803,535

(22) Filed: Jul. 20, 2015

Related U.S. Application Data

(60) Provisional application No. 62/155,769, filed on May 1, 2015.

(51) Int. Cl.
*A61H 1/00* (2006.01)
*A61M 5/42* (2006.01)
(Continued)

(52) U.S. Cl.
CPC ............. *A61M 5/422* (2013.01); *A61B 19/44* (2013.01); *A61B 19/5202* (2013.01);
(Continued)

(58) Field of Classification Search
CPC .. A61B 19/5202; A61B 17/02; A61B 17/24; A61B 17/0206; A61B 1/32; A61B 1/0684; A61M 37/0092; A61M 5/422; A61H 1/00; A61H 13/00; A61H 23/06; A61H 23/0245; A61H 23/0227; A61H 23/0218; A61H 23/02; A61H 23/00
USPC ................... 600/235, 237–245, 249; 604/22; 601/46, 78, 80
See application file for complete search history.

(56) References Cited

U.S. PATENT DOCUMENTS 1,485,963 A 3/1924 Curry
2,247,258 A * 6/1941 Shepard .................... A61B 1/24
116/DIG. 26
(Continued)

FOREIGN PATENT DOCUMENTS

CA 2580792 10/2013
CN 103826686 5/2014
(Continued)

OTHER PUBLICATIONS

International Preliminary Report on Patentability published Mar. 12, 2014 for PCT/US2012/053744.
(Continued)

*Primary Examiner* — Eduardo C Robert
*Assistant Examiner* — Michelle C Eckman
(74) *Attorney, Agent, or Firm* — Paul D. Bianco; Gary Winer; Fleit Gibbons Gutman Bongini & Bianco PL

(57) ABSTRACT

A device vibrates body tissue to reduce pain experience by the body tissue in a therapeutic procedure. The device includes a frame and a tip connectable to the frame which can be activated to produce vibration. An electromagnetic reader is connected to the frame and includes an antenna for sending and receiving electromagnetic radiation. An electromagnetic tag is connected to the removable tip, and also has an antenna for sending and receiving electromagnetic radiation in communication with the electromagnetic reader antenna. The antennas are disposed proximate to each other when the removable tip is connected to the frame, whereby the electromagnetic tag can transmit information to the electromagnetic reader.

21 Claims, 24 Drawing Sheets

(51) Int. Cl.
*A61H 23/02* (2006.01)
*A61B 19/00* (2006.01)

(52) U.S. Cl.
CPC ........ *A61H 23/02* (2013.01); *A61B 2019/448* (2013.01); *A61B 2019/5206* (2013.01); *A61B 2560/028* (2013.01); *A61B 2560/0475* (2013.01); *A61H 2201/0188* (2013.01); *A61M 2205/8206* (2013.01); *A61M 2205/8243* (2013.01)

(56) References Cited

U.S. PATENT DOCUMENTS

| | | | |
|---|---|---|---|
| 2,258,857 A | 10/1941 | McCann | |
| 3,590,232 A | 6/1971 | Sadowski | |
| 3,620,209 A * | 11/1971 | Kravitz | A61M 5/422 601/79 |
| 3,837,595 A | 9/1974 | Boone | |
| 4,091,805 A | 5/1978 | Clark | |
| 4,572,180 A * | 2/1986 | Deenadayalu | A61B 1/227 600/249 |
| 4,593,973 A | 6/1986 | Yoshida | |
| 4,785,796 A * | 11/1988 | Mattson | A61B 1/227 362/109 |
| 4,867,141 A | 9/1989 | Nakada et al. | |
| 5,437,606 A | 8/1995 | Tsukamoto | |
| 5,542,845 A | 8/1996 | Jenkins | |
| 5,636,988 A | 6/1997 | Murayama | |
| 5,639,238 A | 6/1997 | Fishburne, Jr. | |
| 5,647,851 A | 7/1997 | Pokras | |
| 5,647,853 A | 7/1997 | Feldmann et al. | |
| 5,692,900 A | 12/1997 | Fischer | |
| 5,704,902 A | 1/1998 | Vandenbelt et al. | |
| 5,928,170 A | 7/1999 | Garrigan | |
| 5,938,435 A | 8/1999 | Raspino | |
| 5,989,022 A | 11/1999 | Yamamoto | |
| 6,030,210 A * | 2/2000 | Bianchetti | A61C 1/088 433/118 |
| 6,355,007 B1 | 3/2002 | Zuckerbrod | |
| 6,436,035 B1 * | 8/2002 | Toth | A61B 5/0084 362/572 |
| 6,602,229 B2 | 8/2003 | Coss | |
| 6,923,762 B1 * | 8/2005 | Creaghan, Jr. | A61B 5/0059 362/231 |
| 7,244,266 B2 | 7/2007 | Garthe | |
| 7,981,071 B2 | 7/2011 | Goldberg | |
| 8,121,696 B2 * | 2/2012 | Vallero | A61M 5/422 607/46 |
| 8,622,952 B2 | 1/2014 | Goldberg | |
| 8,668,664 B2 | 3/2014 | Goldberg | |
| 8,690,872 B2 * | 4/2014 | Jayaraj | A61B 18/1402 600/249 |
| 2002/0082564 A1 | 6/2002 | Pham | |
| 2003/0040714 A1 * | 2/2003 | Coss | A61M 5/3129 604/187 |
| 2003/0195644 A1 * | 10/2003 | Borders | A47C 31/008 700/90 |
| 2003/0225429 A1 | 12/2003 | Garthe et al. | |
| 2004/0077977 A1 | 4/2004 | Ella | |
| 2004/0254599 A1 | 12/2004 | Lipoma et al. | |
| 2006/0106363 A1 | 5/2006 | Aravena et al. | |
| 2007/0088245 A1 * | 4/2007 | Babaev | A61H 23/0245 604/22 |
| 2007/0145155 A1 * | 6/2007 | Scarlatella | G06K 19/07749 235/492 |
| 2007/0156179 A1 | 7/2007 | Karashurov | |
| 2007/0167943 A1 * | 7/2007 | Janssen | A61B 18/1477 606/41 |
| 2008/0086159 A1 | 4/2008 | Zweifler | |
| 2008/0255483 A1 * | 10/2008 | Goldberg | A61H 7/005 601/72 |
| 2009/0047624 A1 * | 2/2009 | Tsai | A61C 17/20 433/119 |
| 2009/0281464 A1 * | 11/2009 | Cioanta | G06F 19/3481 601/2 |
| 2010/0125172 A1 * | 5/2010 | Jayaraj | A61B 1/06 600/249 |
| 2010/0179457 A1 * | 7/2010 | Blaine | A61M 5/422 601/46 |
| 2011/0054386 A1 * | 3/2011 | Blaine | A61M 5/42 604/22 |
| 2011/0270154 A1 | 11/2011 | Goldberg | |
| 2011/0319812 A1 * | 12/2011 | Goldberg | A61M 5/422 604/22 |
| 2012/0016292 A1 * | 1/2012 | Goldberg | A61H 7/005 604/22 |
| 2012/0029422 A1 | 2/2012 | Goldberg | |
| 2013/0095508 A1 * | 4/2013 | Campitelli | B01L 3/0217 435/7.94 |
| 2013/0197317 A1 * | 8/2013 | Daniel | A61B 1/0684 600/249 |
| 2013/0204202 A1 * | 8/2013 | Trombly | A61M 5/16854 604/207 |
| 2013/0317314 A1 * | 11/2013 | Lampson | A61B 17/50 600/249 |
| 2014/0055588 A1 * | 2/2014 | Bangera | A61J 7/0481 348/77 |
| 2014/0121557 A1 * | 5/2014 | Gannon | A61B 5/002 600/549 |
| 2014/0187870 A1 * | 7/2014 | Weber | A61B 10/0266 600/301 |
| 2014/0188095 A1 * | 7/2014 | Weber | A61B 18/24 606/15 |
| 2014/0188128 A1 * | 7/2014 | Weber | A61B 18/1482 606/130 |
| 2014/0343432 A1 * | 11/2014 | Humayun | A61B 8/10 600/459 |
| 2014/0371542 A1 * | 12/2014 | Goldberg | A61M 5/422 600/249 |
| 2014/0378940 A1 | 12/2014 | Lee | |
| 2015/0134358 A1 * | 5/2015 | Fisher | G06F 19/323 705/3 |
| 2015/0186702 A1 * | 7/2015 | Pletcher | G06K 7/10128 340/686.6 |
| 2015/0216618 A1 * | 8/2015 | Jayaraj | A61B 19/5202 600/249 |
| 2015/0306286 A1 * | 10/2015 | Ross | A61M 1/0037 604/22 |

FOREIGN PATENT DOCUMENTS

| | | |
|---|---|---|
| CN | ZL201080016524.X | 8/2014 |
| JP | S6154832 | 4/1986 |
| JP | 548916 | 6/1993 |
| JP | 2002224183 | 8/2002 |
| JP | 2004129914 | 4/2004 |
| JP | 5549987 | 5/2014 |
| RU | 2011141339 | 5/2013 |
| RU | 2523203 | 5/2014 |
| WO | 03024513 A1 | 3/2003 |
| WO | 2004000196 A1 | 12/2003 |
| WO | 2006/034324 | 3/2006 |
| WO | 2008/042936 | 4/2008 |
| WO | 2010/110823 | 9/2010 |
| WO | 2010/111611 | 9/2010 |
| WO | 2013/036625 | 3/2014 |
| WO | 2015/081181 | 6/2015 |

OTHER PUBLICATIONS

Russian Decision on Granting for Russian application No. 2011141339/02 (061869) dated Mar. 19, 2014.
Japanese Office Action dated Jan. 7, 2014 for JP 2012-502291.
Decision to Grant for JP 2012-502291 dated Apr. 17, 2014.
Columbian Request for Technical Information dated Apr. 12, 2013 for application No. 11-140634.
Response to Columbian Request for Technical Information dated Jul. 15, 2013 for application No. 11-140634.
English translation of Japanese Office Action dated Jan. 7, 2014 for Japanese Patent Application No. JP2012-502291 filed on Sep. 20, 2012.
European Search Report (ESR) for EP application No. 107569266. 1—PCT/US2010028858 dated Aug. 20, 2013.

(56) References Cited

OTHER PUBLICATIONS

For U.S. Appl. No. 13/253,572 Office Actions dated Sep. 17, 2013; Feb. 6, 2014 Responses filed Dec. 17, 2103; May 5, 2014.
Response dated Mar. 24, 2014 to Japanese Office Action for Application No. JP2012-502291 filed Sep. 20, 2012.
Office Action Summary dated Dec. 18, 2013 for MX/a/2011/010069.
International Search Report dated Dec. 13, 2012 for International Patent Application No. PCT/US2012/053943 filed Sep. 6, 2012.
International Preliminary Report of Patentability (IPRP) published Mar. 12, 2014 and Written Opinion (WO) published Mar. 6, 2014 for International Patent Application No. PCT/US2012/053943 filed Sep. 6, 2012.
Russian Decision on Granting a Patent for Invention filed on Mar. 26, 2010 for Patent Application No. RU2011141339 filed May 10, 2013.
Office action dated Jan. 23, 2013 for Israeli application No. 215355.
Response to office action dated Jul. 2013 for Israeli application No. 215355.
Response to Mexican Office Action dated Feb. 4, 2014 for Mexican Application No. MX/a/2011/010069 with English translation.
Office Action dated Mar. 31, 2014 for Mexican Application No. MX/a/2011/010069.
First Office Action for Chinese Application No. 201080016524X with English translation from Chinese associate dated Nov. 20, 2012.
Response to First Chinese Office Action for Application No. 201080016524X dated Jun. 5, 2013.
Second Office Action for Chinese Application No. 201080016524X with English translation from Chinese associate dated Jul. 25, 2013.
Response to Second Chinese Office Action for Application No. 201080016524X dated Dec. 5, 2013.
Third Office Action for Chinese Application No. 201080016524X with English summary from Chinese associate dated Feb. 27, 2014.
Response to the notice prior to examination for Israeli application No. 215355 filed May 12, 2014.
Notice Prior of Allowance dated Jul. 16, 2014 for Israeli application No. 215355.
Ronald Melzack and Patrick Wall, What is Gate Control Theory?, about.com Psychology, 1960.
Jul. 21, 2013 response to Jan. 23, 2013 Office Action for Israel Application No. 215355.
Response dated Mar. 12, 2014 to Office Action dated Sep. 6, 2013 for EP Application 10756926.1.
Response dated May 12, 2014 to third Office Action for Chinese Patent Application No. 201080016524.X.
Supplemental Response filed Oct. 10, 2013 for U.S. Appl. No. 13/179,674.
Office Action dated Sep. 17, 2013 for U.S. Appl. No. 13/253,572.
Notice of Allowance dated Oct. 21, 2013 for U.S. Appl. No. 13/179,674.
Notice of Publication for China application No. 201280043253.6 dated Jun. 5, 2014.
Office Action dated Jun. 25, 2015 for U.S. Appl. No. 13/259,408.
Office Action dated Jun. 4, 2015 for Chinese Application No. 2012800432536.
For U.S. Appl. No. 13/225,782: restriction requirement dated Apr. 26, 2013 and response dated Jun. 26, 2013.
For U.S. Appl. No. 13/179,674: office action dated Oct. 16, 2012; response dated Jan. 16, 2013; final office action dated Mar. 18, 2013; response dated Aug. 19, 2013.
Office Action dated Oct. 16, 2014 for U.S. Appl. No. 13/259,408.
Response Office Action filed Oct. 22, 2014 for Israeli Application No. 215355.
Notice of Allowance dated Oct. 2, 2014 for European Application No. 05 803 150.1-1651.
Notice of Allowance dated Oct. 6, 2014 for Mexican Application No. MX/A/2011/010069.
Official action from European Patent Office for EP 05 803 150.1-1651 dated Nov. 16, 2011.
Response to official action from European Patent Office for EP 05 803 150.1 dated Mar. 26, 2012.
Second official action from European Patent Office for EP 05 803 150.1 dated Feb. 20, 2014.
Response filed with European Patent Office confirming applicant wishes to proceed for EP 05 803 150.1 dated Dec. 20, 2010.
Response to Mexican office action dated Jun. 9, 2014 for Mexican Patent Application No. MX/A/2011/010069.
Australian Patent Examination Report No. 1, dated May 5, 2014 for Patent application No. 2010229783, based on PCT/US10/028858.
Notice of Allowance for U.S. Appl. No. 13/253,572 dated Sep. 18, 2014.
Notice of Publication for HK Application No. 14108064.8 dated Sep. 26, 2014.
Notice Prior to Allowance dated Dec. 31, 2014 for Israeli Patent Application No. 215355.
Supplementary European Search Report dated Jan. 7, 2015 for European Application No. 12829549.
European Communication dated Jan. 23, 2015 for European Application No. 12829549.
Notice of Allowance dated Feb. 13, 2015 for U.S. Appl. No. 13/253,572.
International Search Report and Written Opinion of the International Searching Authority mailed Feb. 25, 2015 for PCT/US2014/67587.
Final Office Action dated Apr. 16, 2015 for U.S. Appl. No. 13/259,409.
Response filed May 21, 2015 to Final Office Action dated Apr. 16, 2015 for U.S. Appl. No. 13/259,409.
Taiwanese Office Action dated May 15, 2015 for Application No. 101132425.
For U.S. Appl. No. 13/225,782: notice of allowance dated Sep. 5, 2013.
International Search Report, Written Opinion dated Nov. 30, 2012 for PCT/US12/53744.
Supplementary European Search Report dated May 18, 2010 for Application No. EP05803150.
International Search Report published on Nov. 2, 2006, for PCT/US2005/33769, filed Sep. 19, 2005.
International Preliminary Report on Patentability published Mar. 20, 2007, for PCT/US2005/33769, filed Sep. 19, 2005.
Written Opinion published on Mar. 20, 2007, for PCT/US2005/33769, filed Sep. 19, 2005.
International Search Report dated Apr. 10, 2008, for PCT/US2007/80262, filed Oct. 3, 2007.
Written Opinion dated Apr. 10, 2008, for PCT/US2007/80262, filed Oct. 3, 2007.
International Preliminary Report on Patentability dated Apr. 7, 2009, for PCT/US2007/80262, filed Oct. 3, 2007.
International Search Report dated Jul. 16, 2010 for PCT/US2009/066033, published Sep. 30, 2010.
Written Opinion dated Jul. 15, 2010 for PCT/US2009/066033, published Sep. 30, 2010.
International Preliminary Report on Patentability dated Sep. 27, 2011 for PCT/US2009/066033, published Sep. 30, 2010.
International Search Report dated Dec. 21, 2010 for PCT/US10/28858 filed Mar. 26, 2010.
Written Opinion dated Dec. 20, 2010 for PCT/US10/28858 filed Mar. 26, 2010.
International Preliminary Report on Patentability dated Sep. 27, 2011 for PCT/US10/28858 filed Mar. 26, 2010.

* cited by examiner

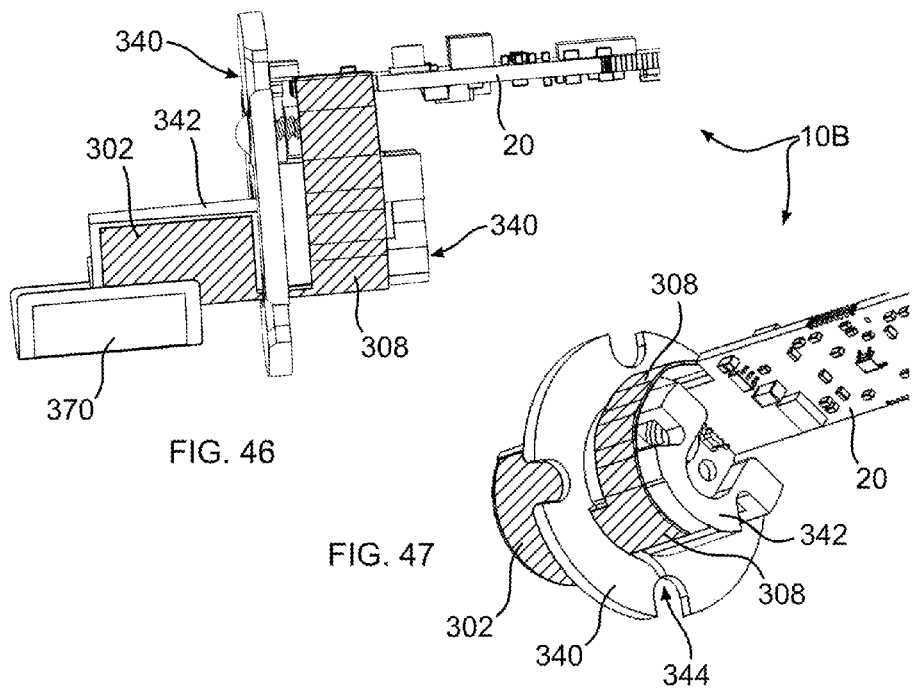
FIG. 46
FIG. 47
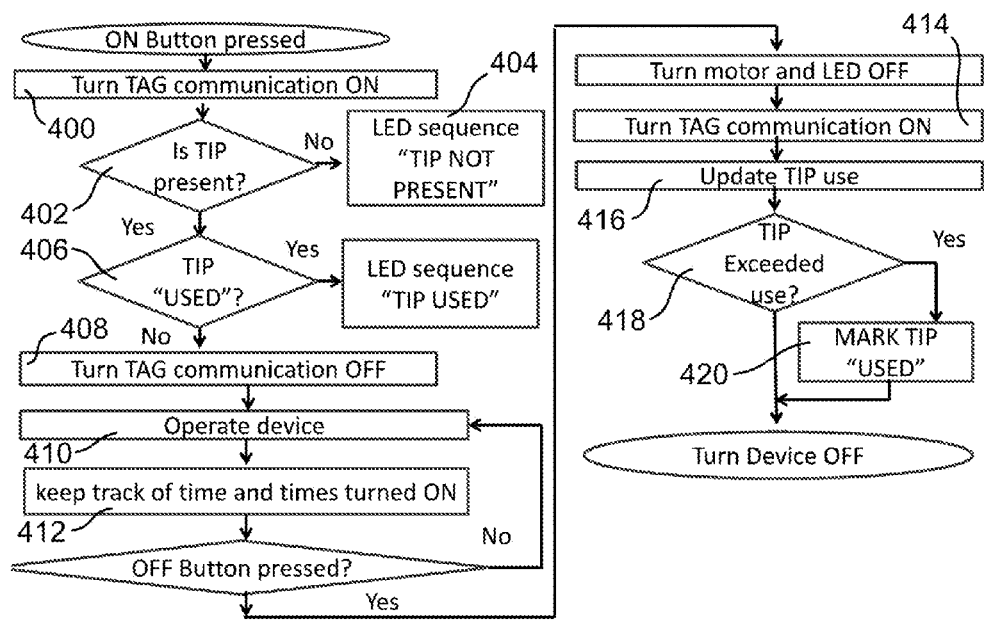
FIG. 48

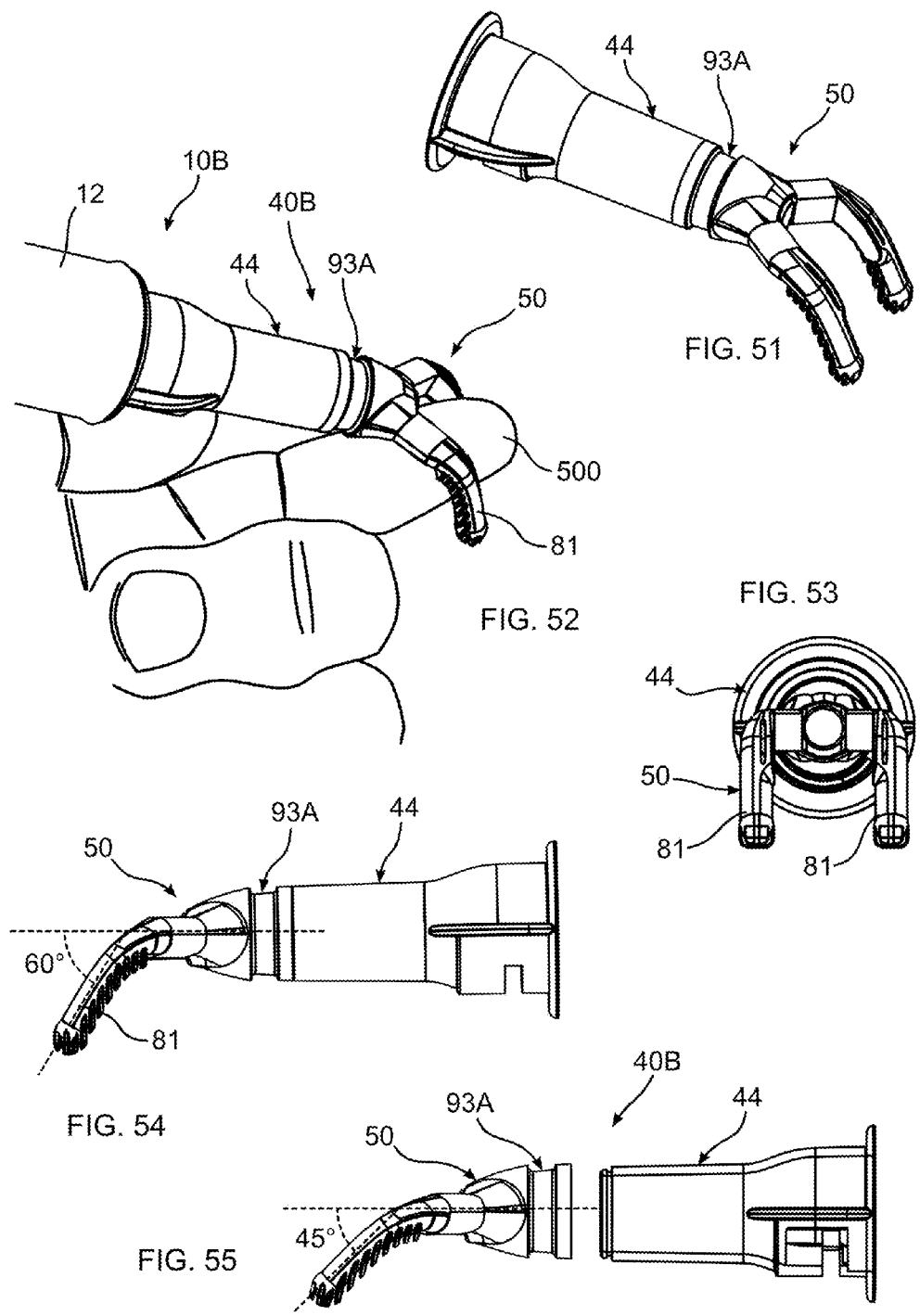

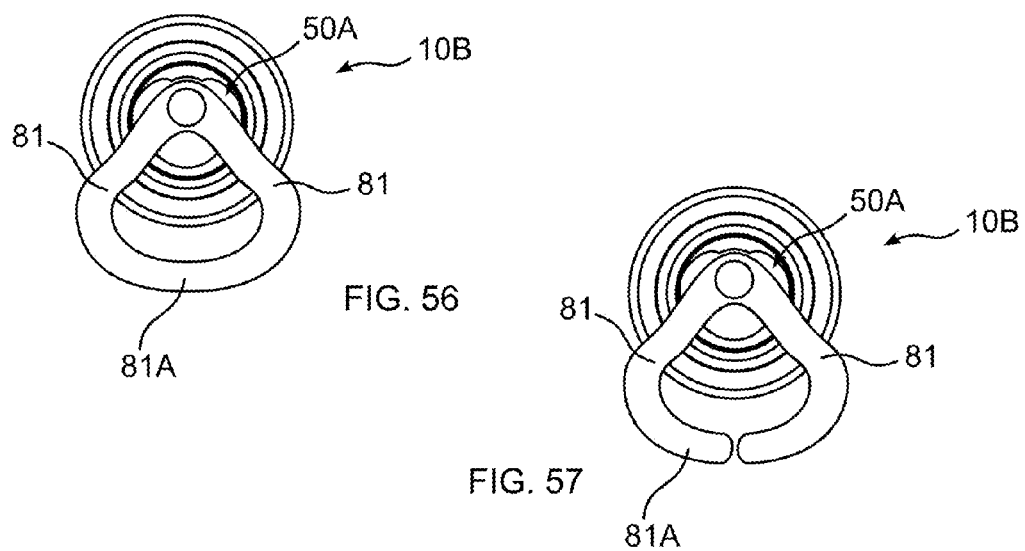
FIG. 56
FIG. 57
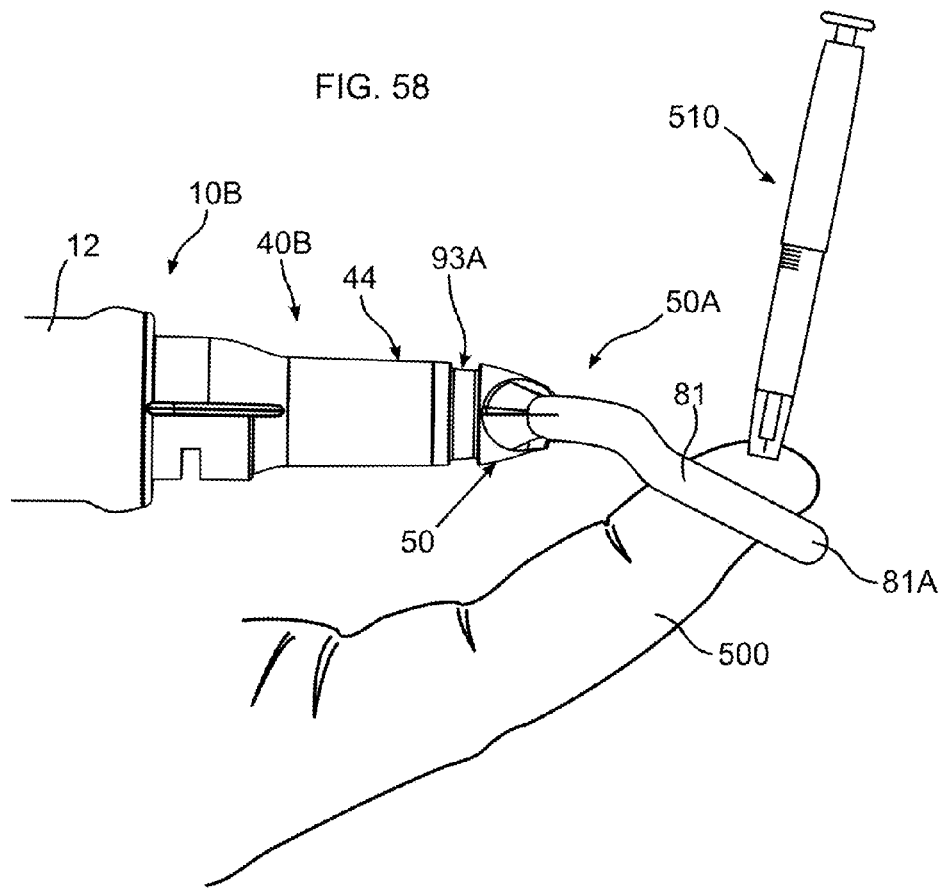
FIG. 58

CONTROLLING USAGE OF REPLACEABLE TOOL ENDS

CROSS REFERENCE TO RELATED APPLICATIONS

This application is related to:
U.S. Patent Application 60/661,497 filed Sep. 20, 2004;
U.S. Patent Application 60/707,754 filed Aug. 12, 2005;
PCT Application PCT/US05/33769 filed Sep. 19, 2005;
U.S. Patent Application 61/163,945 filed Mar. 27, 2009;
PCT Application PCT/US09/66033 filed Nov. 29, 2009;
PCT Application PCT/US10/28858 filed Mar. 26, 2010;
U.S. patent application Ser. No. 13/179,674 filed Jul. 11, 2011, now U.S. Pat. No. 8,668,664;
U.S. patent application Ser. No. 13/225,782 filed Sep. 6, 2011, now U.S. Pat. No. 8,662,95;
U.S. patent application Ser. No. 13/253,572 filed Oct. 5, 2011;
PCT Application PCT/US12/53744 filed Sep. 5, 2012;
U.S. Patent Application 61/531,264 filed Sep. 6, 2011;
PCT Application PCT/US12/53943 filed Sep. 6, 2012;
U.S. Patent Application 61/909,544 filed Nov. 27, 2013; and
PCT Application PCT/US14/67587 filed Nov. 26, 2014, the contents of all of which are hereby incorporated herein by reference in their entirety.

FIELD OF THE DISCLOSURE

The disclosure relates to a system and method for controlling the use of replaceable tool ends, and particular, preventing the use of non-conforming or excessively used tool ends.

BACKGROUND OF THE DISCLOSURE

Procedures for reducing pain when injecting a liquid, such as, an anesthetic, vaccine, or other medically efficacious liquid include (a) to place a very cold material against the skin or flesh of the patient at the injection site, (b) to apply a topical treatment to the skin or flesh at the injection site, which temporarily numbs the skin or flesh or (c) to rapidly manually massage the skin or tissue at the injection site while performing the injection.

SUMMARY OF THE DISCLOSURE

In accordance with an embodiment of the disclosure, a device for vibrating body tissue, comprises a frame; an activatable source of vibration connected to the frame; a removable tip connectable to the frame and having a distal end, the tip connected to the source of vibration when the tip is connected to the frame to thereby vibrate the distal end when the source of vibration is activated; an electromagnetic reader connected to the frame and including a first antenna configured to receive electromagnetic radiation; and an electromagnetic tag connected to the removable tip and including a second antenna configured to send electromagnetic radiation in communication with the electromagnetic reader antenna, the first and second antennas disposed proximate to each other when the removable tip is connected to the frame, the electromagnetic tag thereby configured to transmit information to the electromagnetic reader.

In various embodiments thereof, the device further includes a processor communicatively connected to the electromagnetic reader, the processor configured to execute software stored on non-transitory media, the software configured to store and process information provided by the electromagnetic reader obtained from the electromagnetic tag; processing information includes at least one of: (a) a count of a number of times that the source of vibration has been activated with a unique removable tip connected to the frame; (b) an amount of time that the source of vibration has been activated with a unique removable tip connected to the frame; (c) a number of times that communication has been initiated between the reader and the tag; (d) a number of times that data has been transmitted between the reader and the tag; and (e) a hash function wherein a unique value transmitted by the tag is analyzed to determine authenticity of the tag.

In other embodiments thereof, the first and second antennas overlap at least partially when the tip is connected to the frame; the communication is carried out using an NFC protocol; the electromagnetic tag is a passive style tag; the first antenna projects into an interior space of the tip when the tip is connected to the frame; the second antenna is connected to an interior surface of the tip; the communication is carried out using the ISO/IEC 14443A protocol; the distal end of the tip includes at least two opposing sides forming a space therebetween, the space sized to admit application of a medical device into contact with the body tissue; and/or the device further includes a light configured to shine in a direction of the distal end of the tip when the source of vibration is activated.

In yet further embodiments thereof, the device further includes a motor; a cam connected to the motor; a light source; and a light pipe connected to the light source to transmit light away from the light source, the light pipe connected to the cam to transmit vibration to a distal end of the tip; a battery; a coil connected to the battery, the coil configured to inductive receive electromagnetic energy to charge the battery; the electromagnetic tag includes an electronic component to store data that uniquely identifies the tag, the tag configured to transmit the stored data upon a read request from the electromagnetic reader; the component is configured to store data received from the electromagnetic reader; the data is at least one of: (a) a count of a number of times that the source of vibration has been activated with a unique removable tip connected to the frame; (b) an amount of time that the source of vibration has been activated with a unique removable tip connected to the frame; (c) a number of times that communication has been initiated between the reader and the tag; (d) a number of times that data has been transmitted between the reader and the tag; and (e) a unique value transmitted by the tag that is analyzable to determine authenticity of the tag.

In anther embodiment thereof, processing information includes preventing activation of the source of vibration if at least one of the following conditions are met: (a) a count of a number of times; or (b) an amount of time; that the source of vibration has been activated with a unique removable tip connected to the frame exceeds a predetermined threshold.

In a still further embodiment, the electromagnetic tag includes an electronic component to store data that includes a code useable to validate an authenticity of the tag.

In accordance with another embodiment of the disclosure, an endpiece for vibrating body tissue, the endpiece connectable to a frame having an activatable source of vibration and an electromagnetic reader and antenna, comprises a removable tip releasably connectable to the frame and having a distal end, the tip connected to the source of vibration when the tip is connected to the frame to thereby vibrate the distal end when the source of vibration is activated; and an electromagnetic tag connected to the removable tip and including a tag antenna configured to receive and send electromagnetic radiation in communication with the reader antenna, the tip and reader antennas disposed in proximity to each other when the removable tip is connected to the frame, the electromagnetic tag thereby configured to transmit information to the electromagnetic reader.

In a further embodiment of the disclosure, a method of vibrating body tissue comprises connecting a removable tip to a handheld frame, the tip having a distal end, the tip connected to a source of vibration when the tip is connected to the frame to thereby vibrate the distal end when the source of vibration is activated; and activating an electromagnetic reader connected to the frame and including a first antenna configured to send and receive electromagnetic radiation to read an electromagnetic tag connected to the removable tip and including a second antenna configured to receive and send electromagnetic radiation in communication with the electromagnetic reader antenna, the first and second antennas disposed proximate to each other when the removable tip is connected to the frame, the electromagnetic tag thereby configured to transmit information to the electromagnetic reader.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings, wherein:

FIG. 46 is a side view arrangement of the tag and reader antenna within an instrument of the disclosure, with the nozzle and tip not visible;

FIG. 47 is a perspective view of the reader antenna as installed within the instrument and connected to an electronic circuit board including an electromagnetic reader and a processor;

FIG. 48 is a flow chart depicting an embodiment of flow control for operation of an instrument of the disclosure;

FIG. 51 depicts an alternative replaceable tip of the disclosure including a V-shaped distal end;

FIG. 52 depicts the tip of FIG. 51 connected to a device of the disclosure, applied to a body part of a patient;

FIG. 53 depicts a front view of the tip of FIG. 51;

FIG. 54 depicts a side view of the tip of FIG. 51;

FIG. 55 depicts a side view of the tip of FIG. 51, modified to have an alternative arm angle, and illustrating an alternative non-unitary tip having a separable distal end and base;

FIG. 56 depicts an alternative distal end forming a closed loop;

FIG. 57 depicts an alternative distal end having arms which form a divided loop; and FIG. 58 illustrates the distal end of FIG. 56 used to apply vibration to a body part prior to and during a lancing procedure.

DETAILED DESCRIPTION OF THE DISCLOSURE

Figure 1:
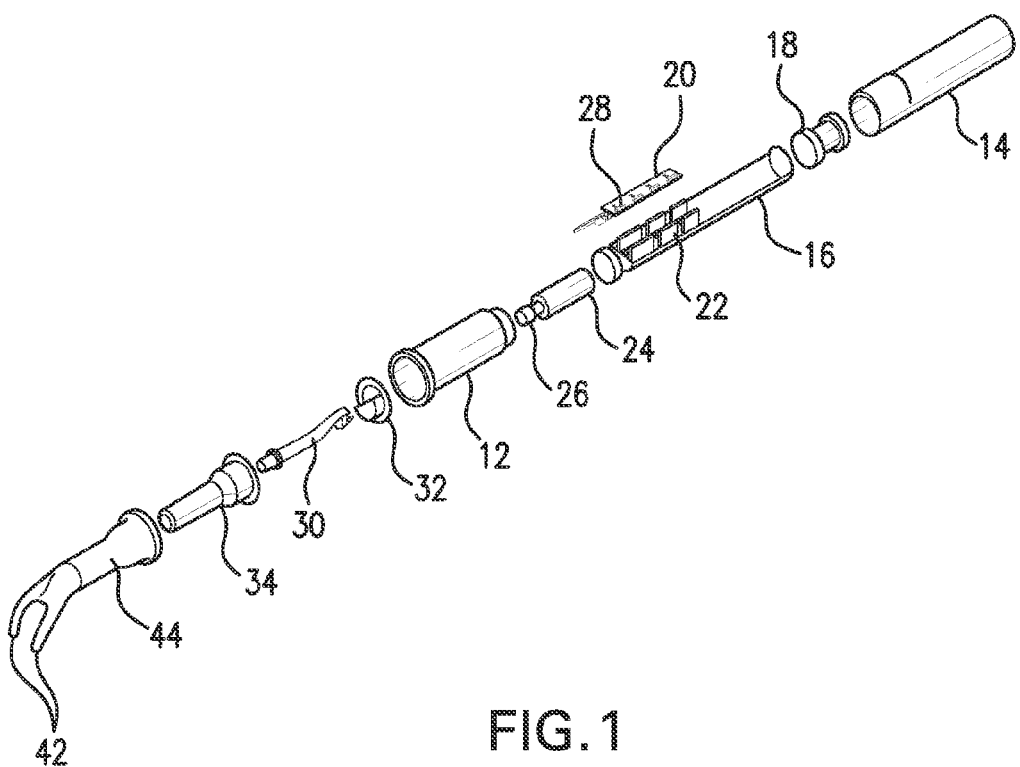
FIG. 1 is an exploded drawing showing an embodiment of the apparatus of the present disclosure.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one, or more than one. The term plurality, as used herein, is defined as two, or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The disclosure reduces pain to a patient being injected, for example with an anesthetic, serum, vitamins, vaccine, or other medically efficacious liquid. The disclosure can be easily and inexpensively utilized during a medical, veterinary or dental procedure to almost completely or substantially eliminate the pain attendant an injection as it punctures the skin or flesh of the patient. The disclosure overcomes the cumbersome, time consuming aspects of the prior art, including providing a more efficacious effect, more often reducing pain to an acceptable level. The disclosure also reduces pain when a body fluid is withdrawn from a patient, for example using a lancet or hypodermic needle and syringe.

The disclosure reduces pain to a patient being injected, for example with an anesthetic, serum, vitamins, vaccine, or other medically efficacious liquid. The disclosure can be easily and inexpensively utilized during a medical, veterinary or dental procedure to almost completely or substantially eliminate the pain attendant an injection as it punctures the skin or flesh of the patient. The disclosure also reduces pain due to any disturbance of the skin our underlying tissues, for example the pain which accompanies puncture of the skin associated with removal of fluids from the body. Examples include while removing blood for a glucose test or other blood analysis; during a puncture associated with treatment of the skin, such as acne or blisters; and for other fluid withdrawals, for example during phlebotomy, paracentesis, aspiration, or synovial fluid withdrawal.

The disclosure provides a disposable tip and a hand-held apparatus, which in an embodiment has the form of an instrument, for vibrating a skin or tissue area. Aspects of the disclosure are described in the incorporated applications. In various embodiments, a vibrating end contacts at least two skin or tissue areas, or a circular skin or tissue area, immediately at an injection site or site of a painful contact, and do so while the painful act takes place. Pain can be caused by injection, for example of a liquid anesthesia, serum, vitamins, vaccine, or other medical or dental efficacious material, into the skin or tissue at the injection site. Typically, a region of interest for a dentist can be the entire oral mucosa area and underlying bone, whereas the region of interest for a medical doctor can be the whole body and underlying bone. The disclosure is applicable to both practitioners, for any area of the body. For a dentist, a typical injection procedure may involve an injection of Lidocaine into a patient's gum or other tissue during a dental procedure.

The method of the disclosure consists in vibrating tissue of a human or animal in proximity to a preselected injection site on the human or animal body while simultaneously injecting by a needle or like instrument a liquid at the preselected injection site. The vibration can be effective if transmitted to a circular or other shaped area of body tissue, which can include bone underlying skin at an injection site, and particularly on opposite sides of injection site.

In various embodiments of the disclosure, reuse of an endpiece such as a vibrating tip of the instrument is prevented, to avoid cross-contamination between patients. In one embodiment, the tip is broken when removed. In another embodiment, electromagnetic communication is established between an electronic tag on a tip and an electronic circuit within the body of the instrument. In this manner, a use count and validation of the tip can be monitored, and activation of the instrument can be disabled if the tip should be replaced after a period of time, or a predetermined number of uses, which are indicative of potential reuse between patients.

The embodiment disclosed herein is a tool for relieving pain associated with an injection. It should be understood, however, that in addition to injections, the disclosure applies to other pain inducing procedures applied to any body tissue, such procedures including cauterizing, application of laser light, application of chemicals, or insertion of sutures, clips, or staples. Further, it should be understood that the disclosure can be used to control the use of any tool tip, whether used in dentistry, general medicine, or within an industrial application, for example a grinding or boring machine tool tip, or other end effector.

Referring to FIG. 1, an embodiment of a vibrating tool is shown generally designated as instrument 10 for performing the functions of the present disclosure, as will be explained hereinafter. In particular, instrument 10 is a handheld apparatus comprising a main frame, body or handle 12 in the shape of a tube having a battery cover 14 as an end closure that is threaded to screw onto the open end of handle 12 in a complementary fit. Handle 12 is composed of hard plastic or other sufficiently rigid material, and partially receives a chassis 22, the uncovered portion being covered by the battery cover 14. One or more rechargeable batteries 14A (visible in FIG. 50) are located in battery compartment 16 of chassis 22. An induction coil 18 is mounted on the end of chassis 22 and positioned in the battery cover 14 to couple to a charge device in a conventional manner. An external power source can be connected to instrument 10 by a wire, to charge an internal battery, to power the device in the absence of a battery, or to power the device while a battery is charging.

Figure 23:
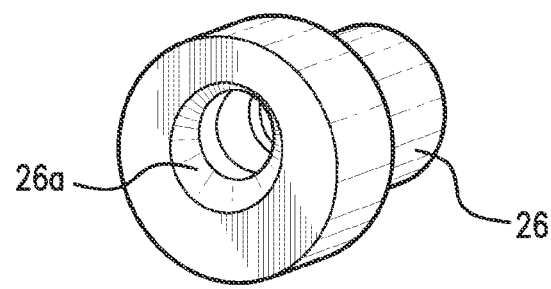
FIG. 23 is a perspective view of the cam attachment to the electric motor to induce vibrations.

A motor 24 driving a cam 26 is housed in the handle 12. Cam 26 includes a bore, see FIG. 23 (in the form of a ball socket 26a) whose axis is offset from the motor drive axis by from about 0.010 inches to about 0.025 inches, with an offset of about 0.020 inches, for example, being effective. The vibration induced by the cam 26 and follower 100 is transmitted via a polycarbonate light rod 30 to polycarbonate tip frame 50 and will produce vibrations at the free ends of the two bifurcated legs 42 of tip frame 50 having amplitude of about 0.5 mm (0.020 inches). It should be understood that polycarbonate can be replaced with any other material of sufficient rigidity and light transmitting ability. It should further be understood that alternative means of producing vibration can be provided, including for example reciprocating mechanisms, electromechanical actuators, and acoustic or other vibrating transducers, or other types, as known or hereinafter developed.

During vibration, the light rod 30 pivots about a resilient mounting, enabled in an embodiment by a resilient O-ring, at the end of nozzle 34 which can hold the light rod 30 relative to nozzle 34 so that it can vibrate freely. A PCB board 20 containing electrical and electronic circuitry 28 is mounted on the chassis 22. The battery is connected via the circuitry 28 to control the motor 24 in the manner described in one or more of the prior applications incorporated herein by reference. When the motor 24 is driven, vibration produced by the cam 26 is coupled to polycarbonate light rod 30 via a coupling fitting and cam follower.

Figure 2:
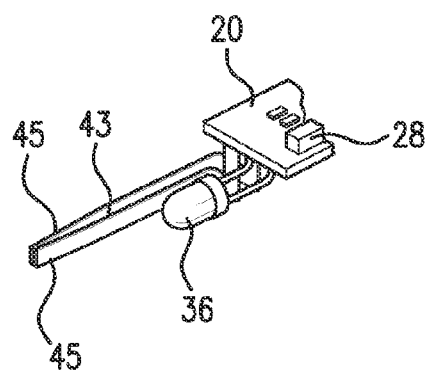
FIG. 2 shows in perspective details of the LED and electrical interlock switch.

The forward end of the handle 12 has an adapter 32 fixed to the chassis and the handle. A nozzle 34 is fixed to the adapter 32. The light rod 30 is received in the nozzle 34 and is resiliently coupled to it at its forward end. The nozzle 34 receives an endpiece, in this embodiment a disposable tip 40 comprised of three components, namely, a forward vibratable tip 50 detachably and rigidly mounted on the end of light rod 30 to transmit vibrations, with tip 50 having, among various configurations, a bifurcation at its forward end; a tip sleeve 62 for detachably and rigidly mounted on nozzle 34; and an overmold 52 that holds tip 50 and sleeve 62 together and enables tip 50 to vibrate freely relative to sleeve 62. An LED 36 is mounted to the PCB 20 as shown in FIG. 2, disposed to transmit light into light rod 30 during vibration of light rod 30.

Additionally projecting forwardly from PCB 20 is electrical interlock 43 extending forwardly and consisting of two spring electrodes 45 normally biased apart to leave a small space between them. When the two electrodes 45 are brought together, they enable an electrical circuit that drives motor 24. There is also a master switch 46 in the electrical circuit that controls overall power for the unit and is incorporated with button 48 (see FIG. 9) resiliently mounted in the handle 12.

Figure 3:
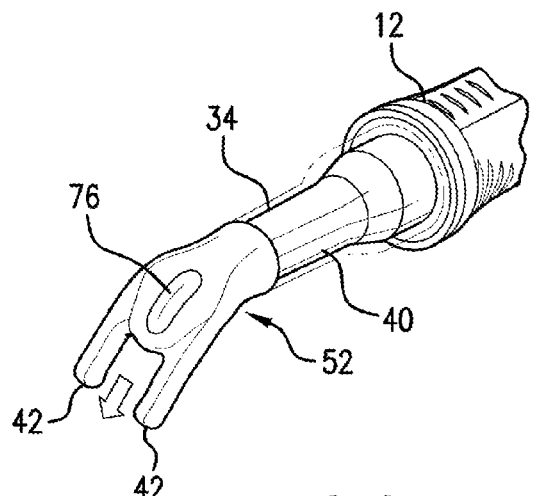
FIG. 3 shows in perspective the removable or disposable tip on the end of the instrument.
Figure 4:
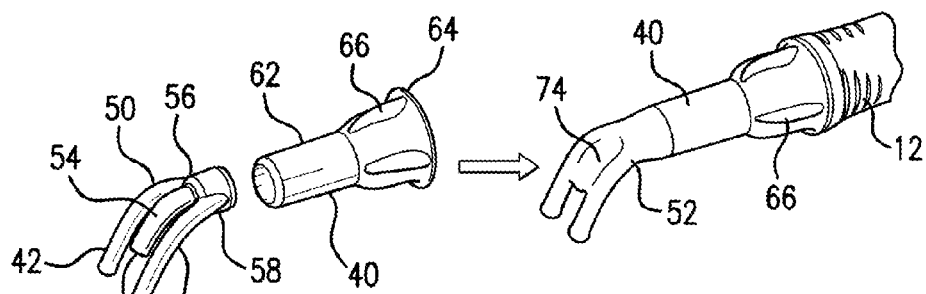
FIG. 4 shows in perspective the removable tip and the end of the instrument.
Figure 5:
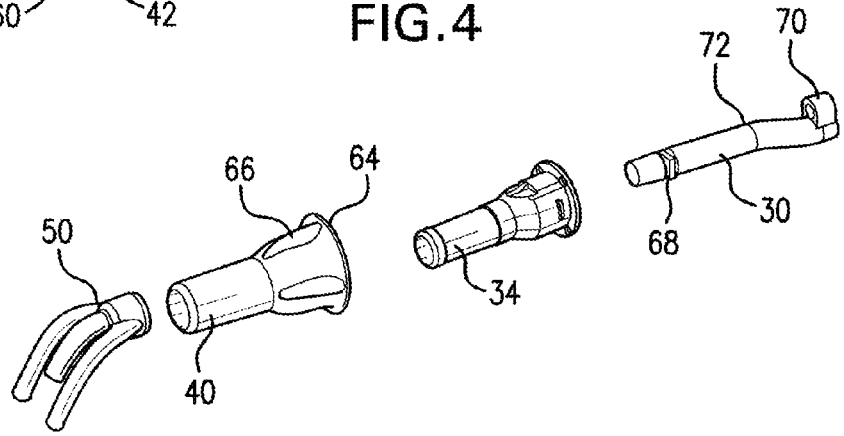
FIG. 5 shows in perspective the light-transmitting rod in relation to the removable tip on the end of the instrument.

FIGS. 3, 4 and 5 show various details of the disposable tip 40 mounted on the nozzle 34. As shown the forward end of the disposable tip 40 is a frame 50 overmolded with plastic 52, advantageously resilient or with a soft finish as it will lie adjacent the tissue surrounding the injection site. Alternatively, it can molded completely of plastic or other suitable biocompatible material.

Between the two legs 42 of the bifurcation there is a cantilevered light extending tube 54 extending from a hole 56 at the junction with the base 58 of the bifurcation of the frame and terminating in a lens 60. This tube can be eliminated as shown in FIGS. 24 to 28. The overmold 52 holds the tip frame 50 to the remainder of the tip 40 consisting of annular body 62 (tip sleeve) that terminates on its rear end with a flange 64 reinforced with ribs 66. The overmold enables the frame 50 to vibrate freely relative to sleeve 62.

The forward end of the light rod 30 fits in nozzle 34 with the O-ring held by wedges 35 received in groove 68 to center the light rod 30 in nozzle 34 and light rod 30 projects from the forward end thereof and is received in the rear end of the overmolded bifurcation (tip frame 50) in tight engagement to impart vibrations from the light rod 30 to the tip frame 50. Light rod 30 is in alignment with hole 56 to transmit light through hole 56 and, optionally, tube 54 through lens 60 onto the injection site.

In FIG. 5 the light tube 30 is shown with a circumferential groove 68 adjacent its forward end (to receive a resilient gasket, O-ring) and a coupling fitting member 70 at is other end. Light tube 30 has a bend 72 toward its rear that offsets the axis laterally so that it will align with the LED 36. As shown in FIG. 4 the overmold 52 of the bifurcation has horizontal grooves 74 to collect saliva if used in the mouth. Likewise in FIG. 3, the bifurcation can have a downward extending groove or reveal 76 for the same purpose. Removal of the saliva is difficult and this helps to prevent reuse of the tip.

Figure 16:
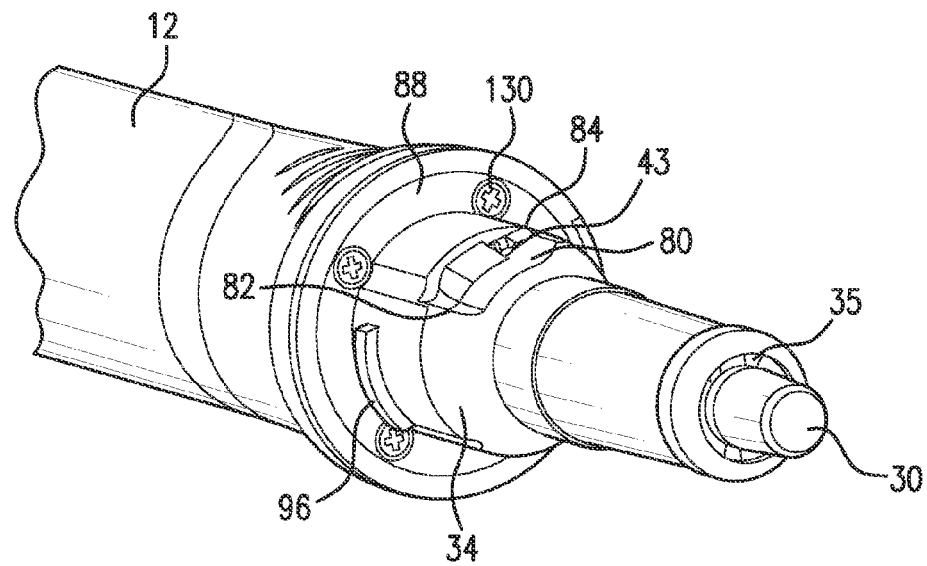
FIG. 16 shows in perspective the handle and nozzle of the instrument.
Figure 17:
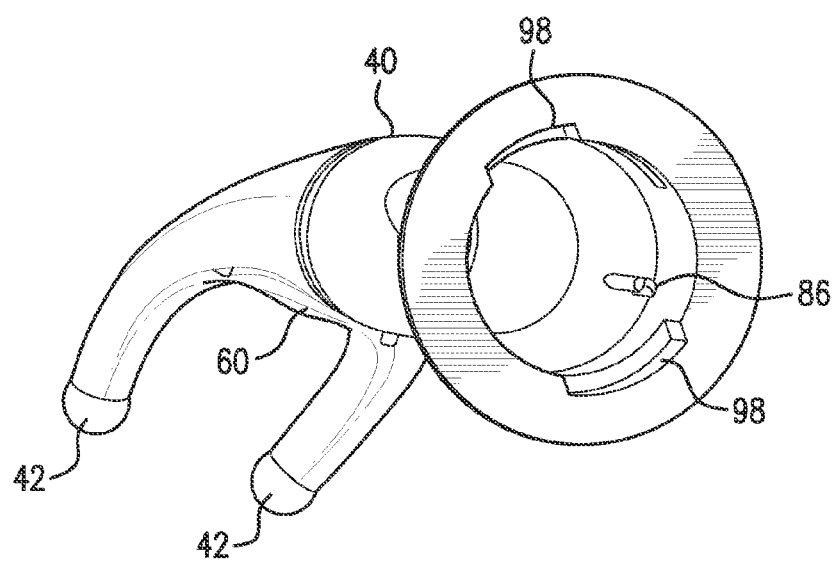
FIG. 17 shows in perspective the disposable tip seen from the rear.

FIGS. 6, 7, 8 and 12 show one way for positively preventing the disposable tip 40 from a second use. See also FIGS. 16 and 17 in this regard. The electrical interlock 43 is brought out onto the surface of the nozzle 34 at a cutout 80 with the two electrodes 45 lying one above the other with a small space between. A ramp 82 is formed adjacent the cutout area 80 and the transition between the ramp 82 and the cutout 80 is a vertical (90 degree) flat surface 84. The sleeve 62 of disposable tip 40 is provided on its inner surface with a frangible rib 86 that coacts with ramp 82, interlock 43 and flat surface 84 as follows.

The disposable tip 40 is mounted to the nozzle by placing tip 40 over nozzle 34, seating tip 40 and giving tip 40 a one quarter turn. The orientation and alignment of these two parts is such that the rib rides over the ramp 82, and drop down over the flat surface 84 onto the electrical interlock 43, forcing the two electrodes 45 together to enable actuation and vibration of instrument 10. When the tip 40 is to be removed, the tip is given a reverse one quarter turn, during which rotation the frangible rib 86 will strike the vertical surface 84 and be broken off as the tip continues completing the one quarter turn necessary to disengage from nozzle 34. Thus, after the tip 40 has been removed, it will no longer be able to be replaced on the nozzle 34 and to cause electrical interlock 43 to function.

Figure 6:
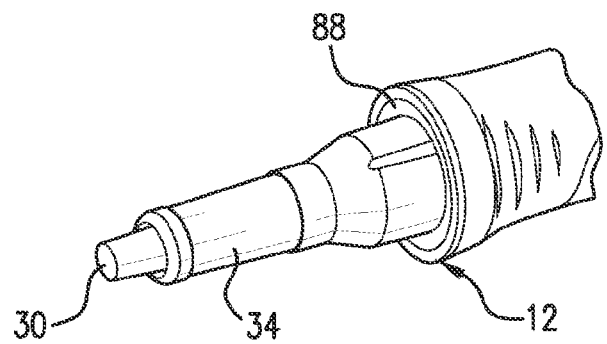
FIG. 6 shows in perspective the end of the instrument.
Figure 8:
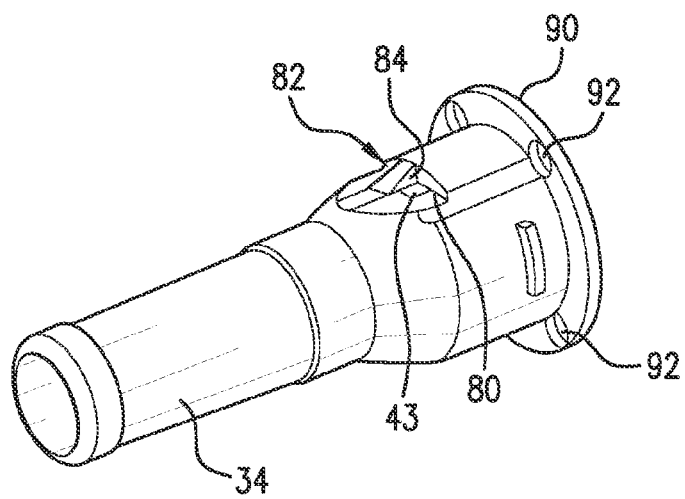
FIG. 8 shows in perspective the nozzle of the instrument.

FIG. 8 also shows that the rear end of the nozzle 34 has a flange 90 with openings 92 to enable attachment to the chassis 22 and handle 12. As shown in FIG. 6, a cover ring 88 covers the flange of the nozzle 34.

Figure 9:
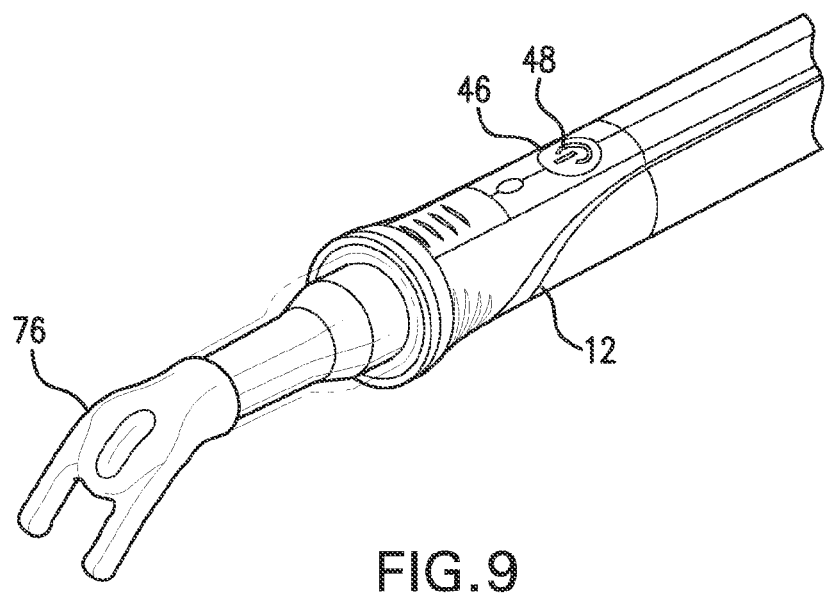
FIG. 9 shows in perspective a top view of the instrument.
Figure 10:
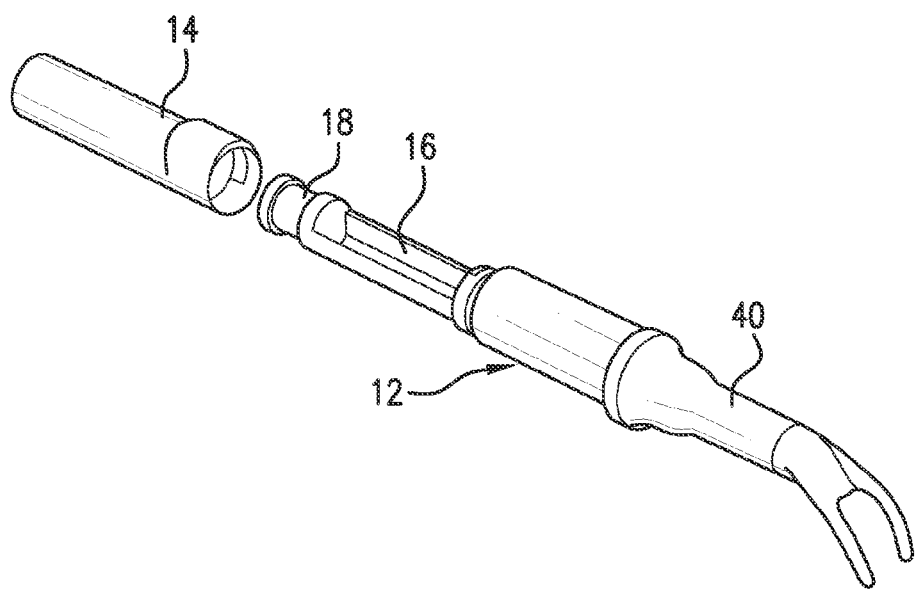
FIG. 10 shows in perspective a partially exploded view showing the instrument with the battery cover removed.
Figure 11:
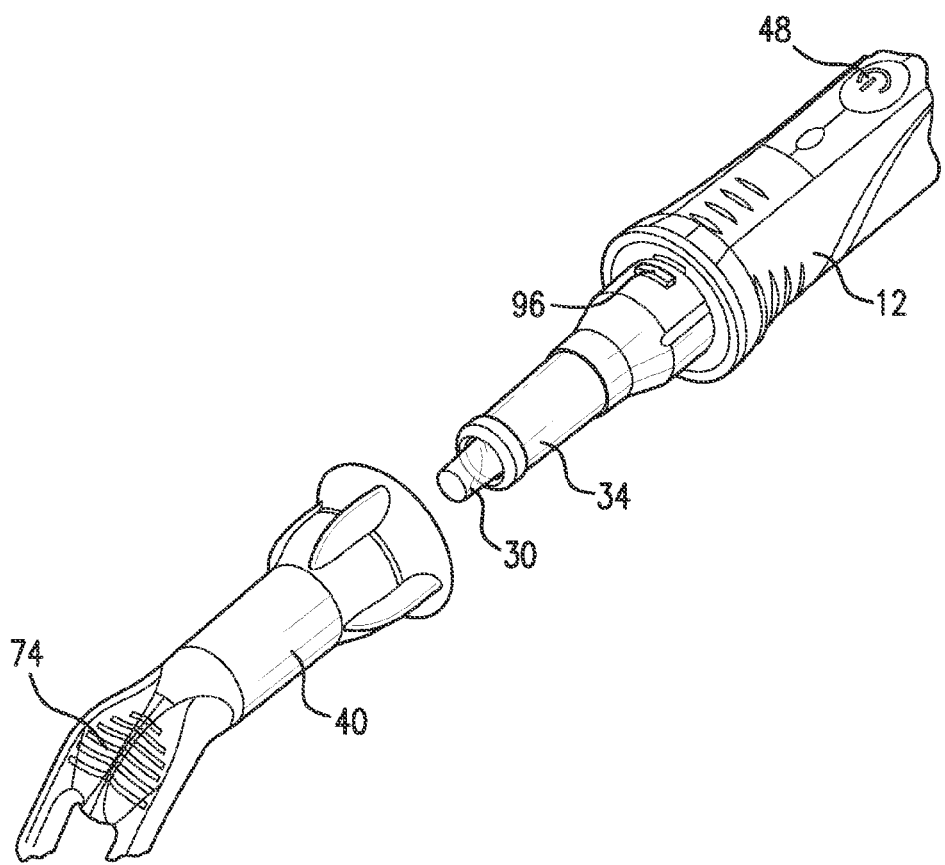
FIG. 11 shows in perspective grooving on the disposable or removable tip.

FIG. 9 shows the device or instrument assembled with a master switch 46 mounted on the handle 12 beneath a resiliently mounted button 48. FIG. 10 shows the battery cover 14 removed and the battery compartment 16 exposed. The battery compartment is part of the chassis 22. FIG. 11 is a view similar to FIG. 10 but showing the front end of the device or instrument and illustrating the relationship of the disposable tip 40 to the light rod 30 and nozzle 34. A circumferential rib 96 and groove 98 are formed diametrically opposite on the nozzle 34 and coact with a complementary circumferential groove 98 and rib 96 (see FIG. 12) in the inner surface of the tip 40 to lock the tip on the nozzle in a bayonet fitting.

Figure 13:
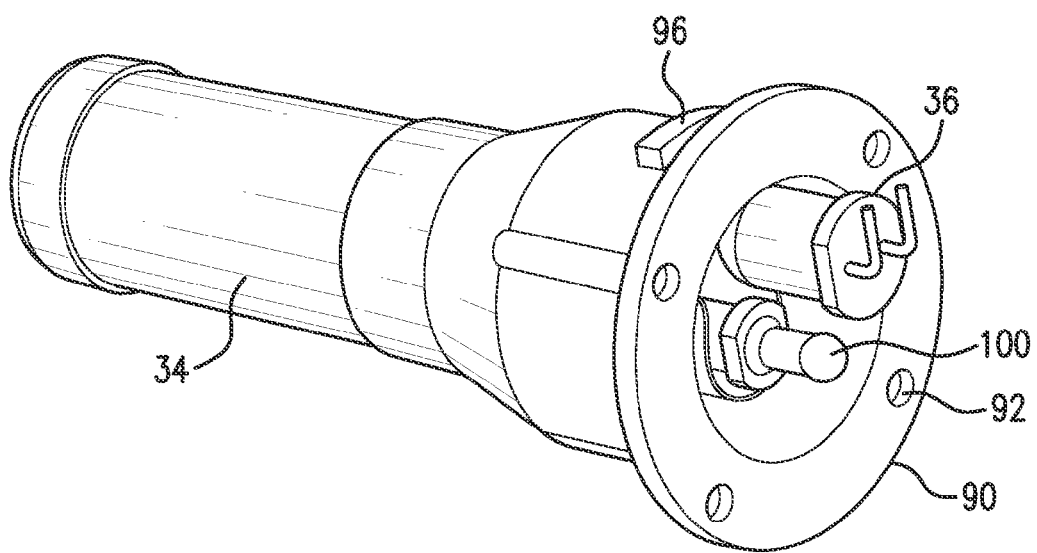
FIG. 13 shows in perspective the rear end of the nozzle.

FIG. 13 shows the rear end of the nozzle 34 from which the fitting member 70 attached to the end of the light rod 30 and holding a projecting stub with ball end 100 as a cam follower for contacting and following the cam 26 (see FIG. 23 for detail) to impart the vibratory motion of the cam 26 to the light rod 30. The bottom of the light rod 30 is in alignment with the LED 36 as previously described. Although continuous pulsing can be used, it has been discovered that a pulsed vibration sequence is more effective. A pulsed sequence of about one second on and then about a tenth of a second off, is sufficient to pulse the vibration without allowing the vibration of the tip to ever drop down to zero. In this manner, the device or instrument pulses about every second, re-stimulating the nerves in the area. Without being bound to any theory, it appears that by cycling or pulsing as described, the brain does not get accustomed to, or habituate to the vibration, and thus the vibrations remain effective. Other patterns and durations of pulsing or cycling can be used, as best determined by the practitioner as observed to reduce habituation to the vibration among various patients or patient demographics. To this end the electronics controlling the pulsing is modified to include the necessary means for pulsing and obtaining the desired on/off duty cycle as noted. The motor is energized using 110 volt AC (110 Hz frequency). The frequency can vary from about 100 Hz to about 300 Hz. The vibration at the free ends of the prongs or forks 42 can vary from about 0.1 mm to about 0.75 mm. The duty cycle on pulsing is about 0.908 Hz (cycle time=about 1.1 sec. with a pulse off of about 0.1 sec. The off portion of the cycle is advantageously not greater than about 0.5 sec if it is desired to avoid substantial diminution of vibration.

Figure 14:
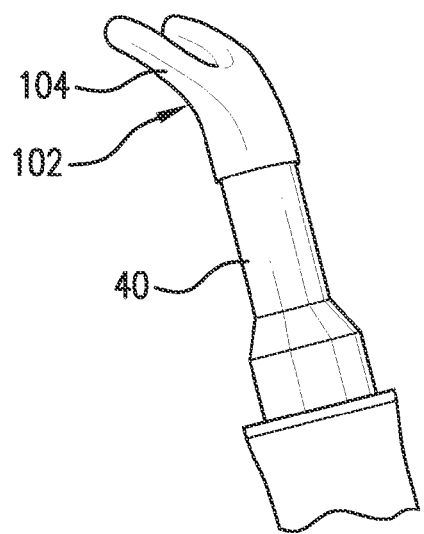
FIG. 14 shows in perspective the removable tip.

FIG. 14 shows in perspective the bifurcated end of the device and illustrates the profile. Essentially the overmolded tip runs straight (102) before it curves downwardly (104) at the bifurcated prongs 42, in order to obtain greater light being shined on the injection area of the tissue. The fact that this device exhibits enhanced amplitude and percusses the tissue contacted, causes a deeper penetration of the vibratory stimulus into the oral mucosa of a dental patient, thereby stimulating the nerve receptors, for example A-beta nerve receptors, which are located deep within the tissue. Additionally, vibration is transmitted in a full 360 degrees around the tip 40, mainly, from three places off of the tip, and specifically, from each free end of the fork 42, as well as from the paddle or retractor portion (area between tips of forks or prongs and joint with tip sleeve 62, which at times can stimulate the lip or cheek or bone when resting against it.

Figure 29A:
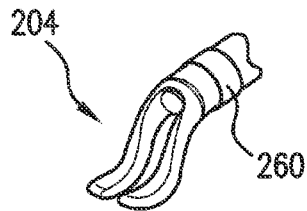
FIGS. 29A-M show in perspective views different tip shapes for the tip member shown in FIGS. 24-26.
Figure 29B:
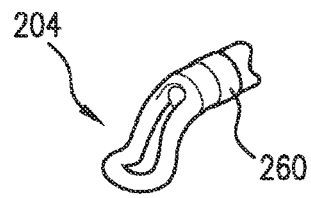
Figure 29C:
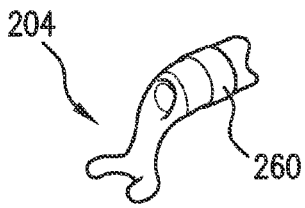
Figure 29D:
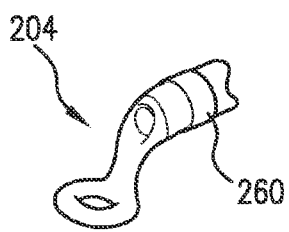
Figure 29E:
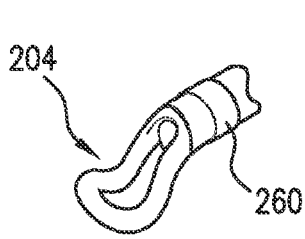
Figure 29F:
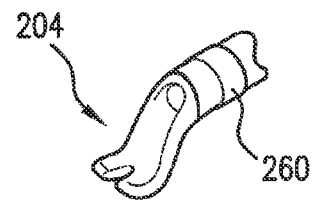
Figure 29G:
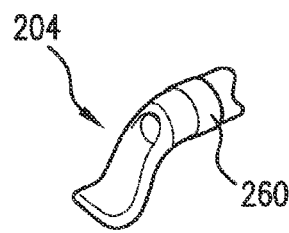
Figure 29H:
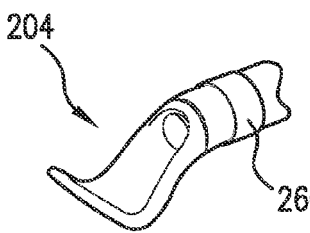
Figure 29I:
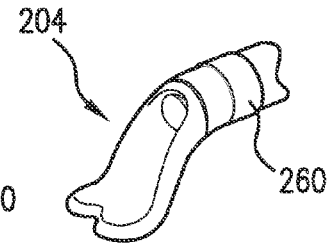
Figure 29J:
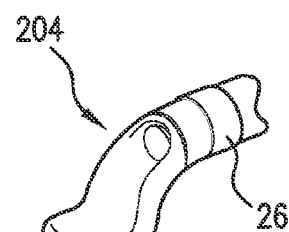
Figure 29K:
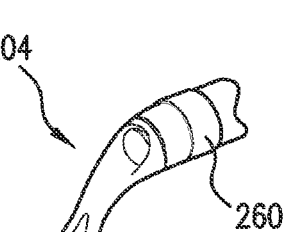
Figure 29L:
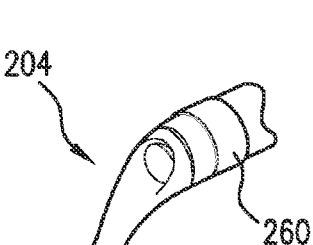
Figure 29M:
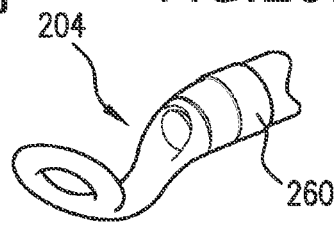

The enhanced vibration is not limited to just in between the two forked prongs 42. Alternative tip free end shapes are shown in FIGS. 29*a-m*. FIG. 29*a* shows a bent fork, FIG. 29*b* shows a bent loop, FIG. 29*c* shows a bent flat U-shape, FIG. 29*d* shows a bent flat circular shape, FIG. 29*e* shows a bent loop, FIG. 29*f* shows a bent flat with a V-groove, FIG. 29*g* shows a bent flat plate, FIG. 29*h* shows a bent up plate, FIG. 29*i* shows a bent flat heart shape, FIG. 29*j* shows a bent flat rounded plate, FIG. 29*k* shows a downward member with a top groove, FIG. 29*l* shows a downward rod with a terminal bulb and FIG. 29*m* shows a bent up circular loop.

Accordingly, in various embodiments, a distal end of tip 40 includes at least two opposing sides with a space between them, whereby a needle or other medical device can be applied to body tissue between the opposed sides. Without being bound to a particular theory, this is believed to improve a likelihood that vibration will be applied to nerves located near a locus of potential pain, where the medical device is applied, to thereby alleviate pain.

Figure 15:
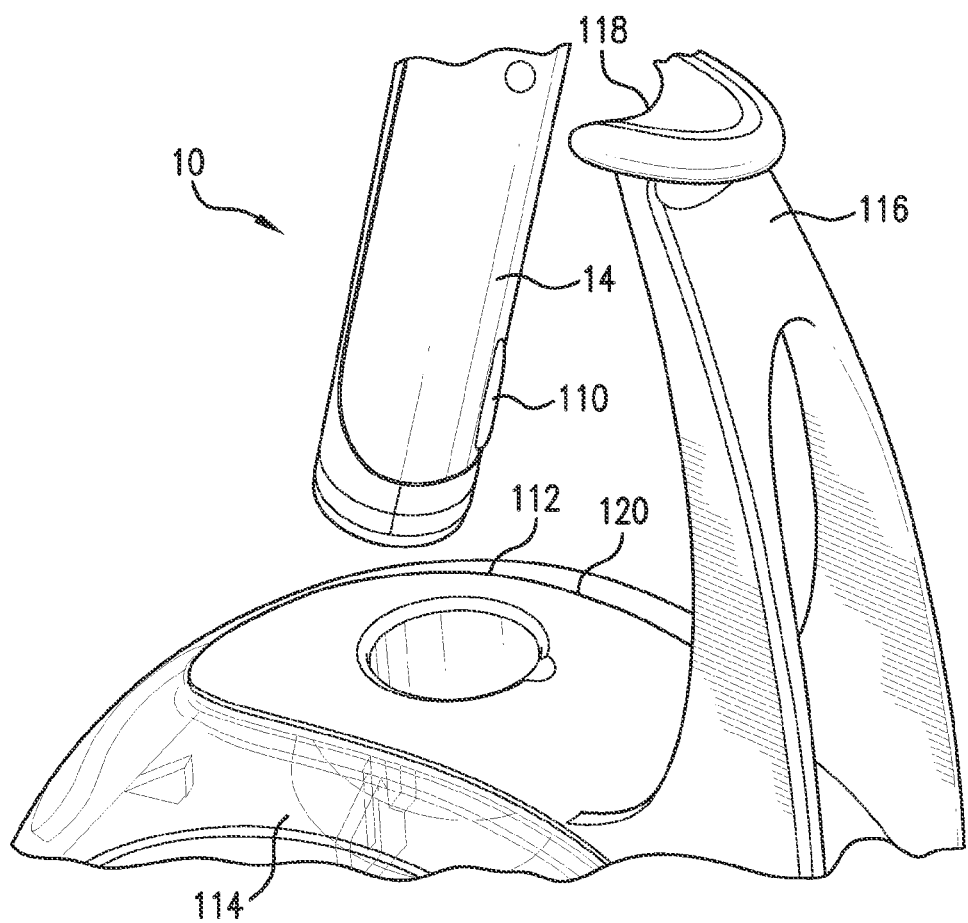
FIG. 15 shows in perspective in partially exploded view the instrument of the disclosure during non-use, positioned in a charging base to be recharged.

FIG. 15 shows a simple mount for storing the device or instrument between uses. The rear end of the battery cover 14 is provided with a rib 110. The rear end of the device is inserted in a well 112 in a stand 114 that has a recess 120 extending downwardly to mate with the rib 110 for orientation purposes. The stand 114 can have a vertical support 116 that terminates in a curved cradle 118 to receive and hold the forward part of the device or instrument 10. Alternatively, the instrument can be supported by a mating fit between an end of the instrument and well 112. The stand is provided with means to connect to a power source to charge the batteries in the device 10 via induction in a manner well known in the art. A plug in cord can alternatively be used, to powering the instrument with 110*v* or 220*v*, for example, wherein the higher voltage power can be converted to a lower voltage, and/or can be converted to direct current, prior to being passed into the instrument, or the conversion can be carried out within the instrument.

Figure 18:
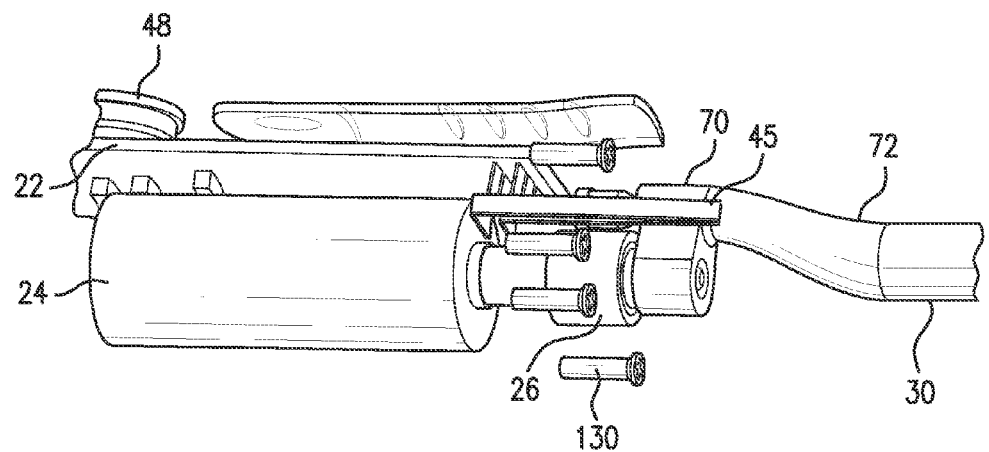
FIG. 18 is a partial view in perspective showing the motor mount and coupling with the light rod.
Figure 19:
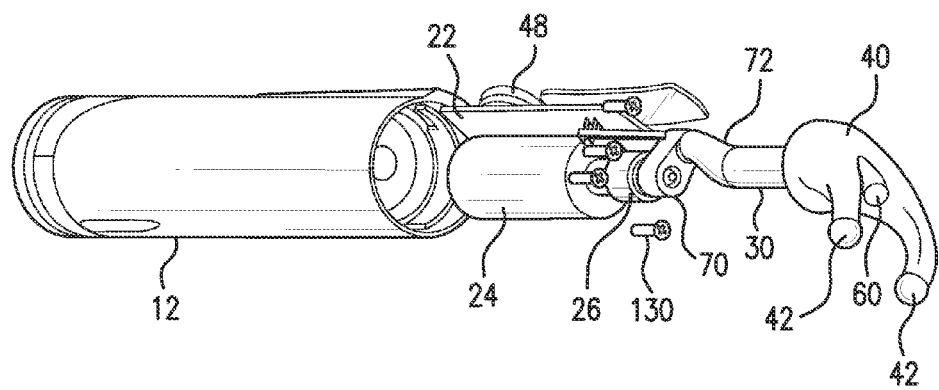
FIG. 19 shows in perspective in partially exploded view the handle, motor and coupling to the light rod and tip illustrating the light port.
Figure 20:
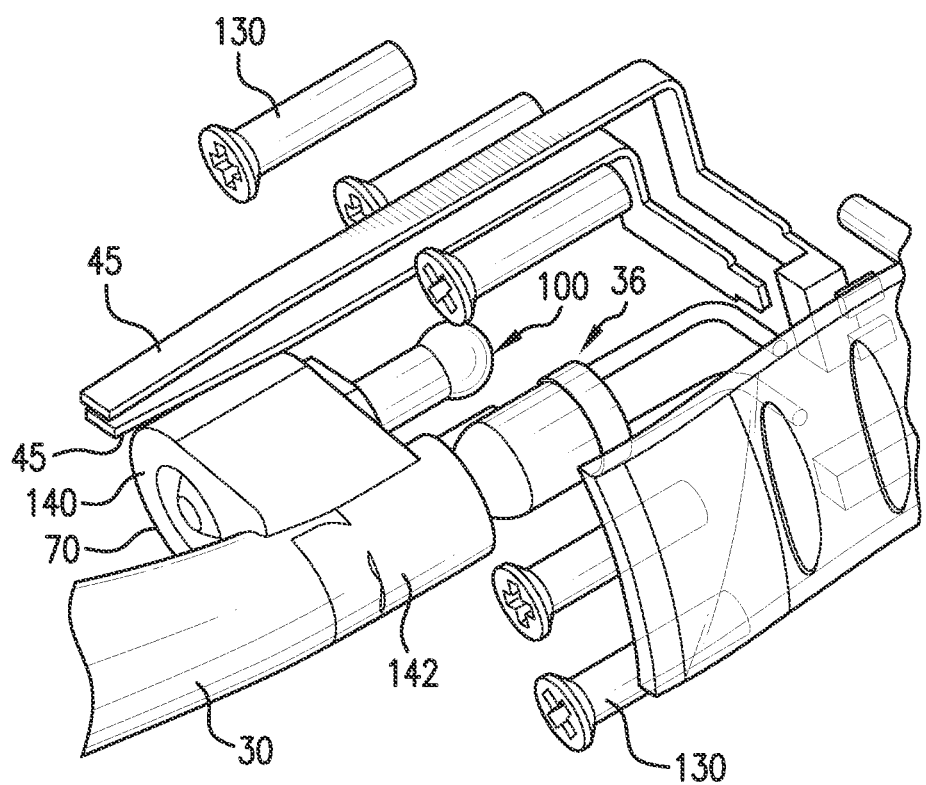
FIG. 20 is a view in perspective showing in an exploded view details of the coupling member on the inner end of the light rod.

FIGS. 18, 19 and 20 show details of the structure and the function of the device or instrument 10. Shown in FIG. 18 is the motor 24 mounted to the chassis 22 with the motor shaft connected to and driving the cam 26, The attachment fitting member 70 fixed to the light rod 30 is shown with the projecting stub with ball end 100 received in the cam 26. Light rod 30 is shown with bend 72 to displace its axis laterally so that the end of the light rod is aligned with LED 36.

The electrical interlock is shown extending forwardly. The button 48 with switch 46 is shown in juxtaposition to the chassis 22 and the PCB positioned on to of the chassis. Screws or bolts 130 are shown and connect the nozzle 34 to the chassis 22. FIG. 19 adds the detail of the assembly shown in FIG. 18 being inserted into the handle 12 and the bifurcation member 42 in juxtaposed relation to the end of the light rod 30. FIG. 20 is an exploded view showing the above described relationships in even more detail.

The attachment fitting 70 consists of an annular member 140 that captures and holds, advantageously rotatably, the projecting stub with ball end 100. The member 140 is held on the end of the light rod 30 by a band 142 that clamps it to the rod 30.

There may also be contained within the handle 12 a music recorder/player that is loaded with a recording that plays through a speaker situated in the handle behind perforations. A switch can be provided suitably connected to turn the recorder/player on/off.

As shown in the incorporated references, the device or instrument 10 can be combined with a toy 160 in a manner useful for distracting children while performing an injection. For children, the disposable tips are sized appropriately, and the vibration is reduced appropriately. The toy 160, for example, is a finger puppet, such as a thumb animal that is hollow inside and open at the rear. The toy can be mounted on the charging end of instrument 10. When the procedure is finished, the toy 160 can be removed and the toy given to the child to help calm the child. Any suitable toy can be used for this purpose, such as a doll, a fire truck and the like, as long as it can connect to instrument 10 in a detachable manner.

Figure 21:
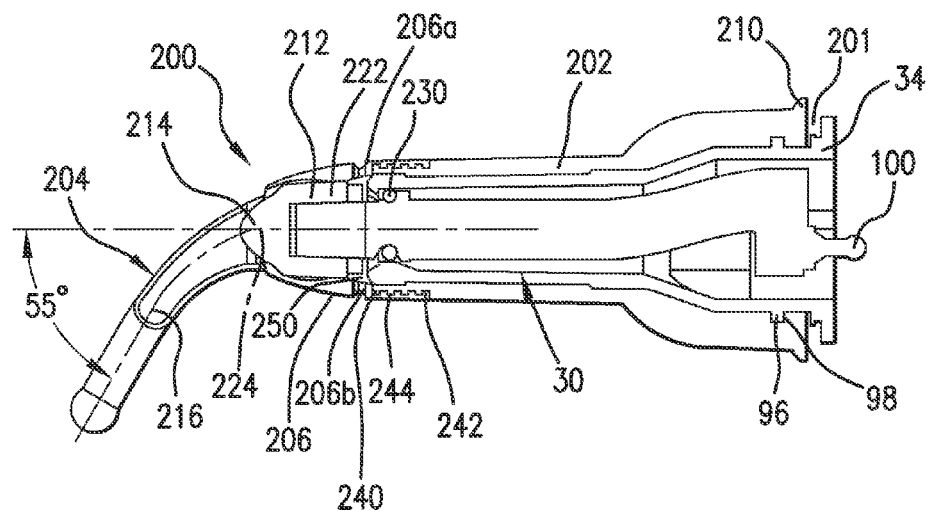
FIGS. 21 and 22 show in cross section and perspective, respectively, details of an embodiment of the present disclosure showing an instrument in the form of a instrument and an article in the form of a single use or disposable tip for use in a method for medical and dental procedures, said improvements contributing for reducing or minimizing pain during tissue or skin puncturing procedures, such as, administration by injection, into the gums, skin or other tissue of a patient, of a liquid, such as, and in particular, an anesthetic.
Figure 22:
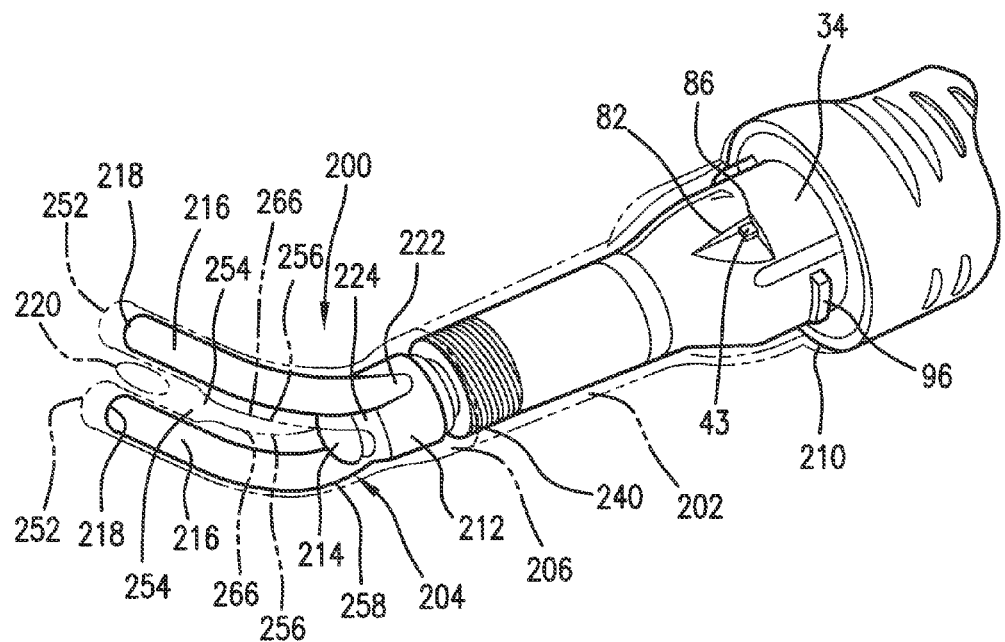
Figure 24:
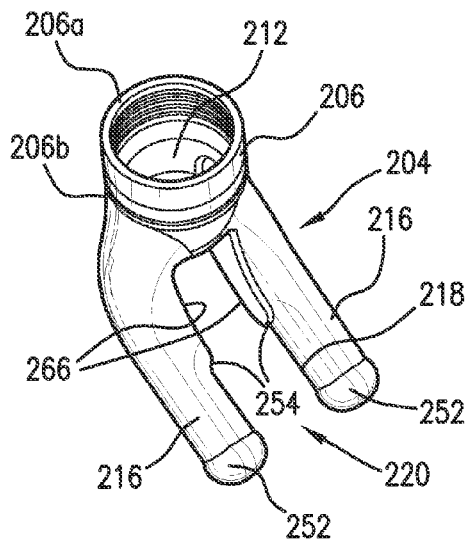
FIGS. 24-26 show in perspective and side views the vibrated tip member.
Figure 25:
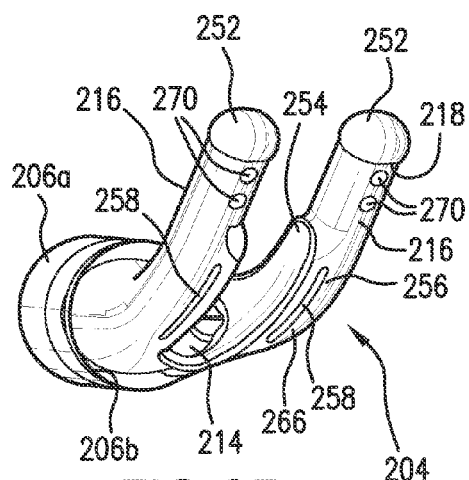
Figure 26:
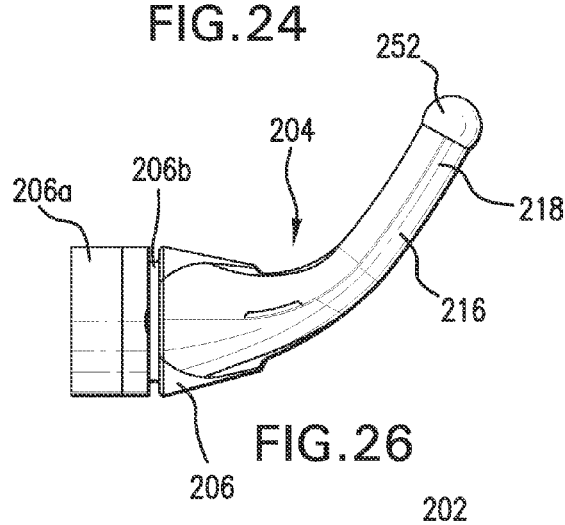
Figure 27:
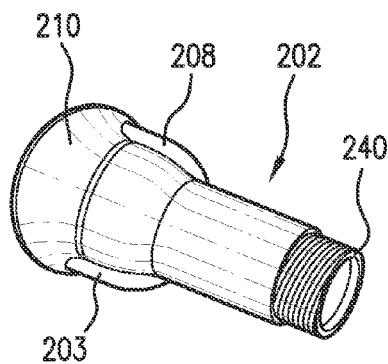
FIGS. 27 and 28 show in side views the tip sleeve.
Figure 28:
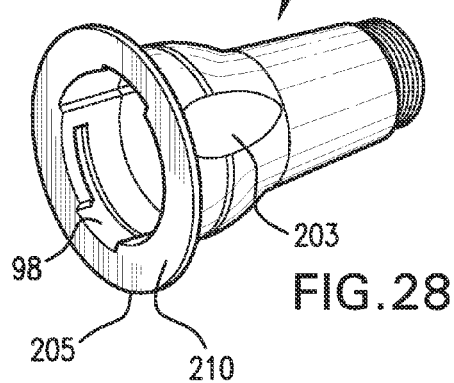

An embodiment of the single use or disposable tip is shown in FIGS. 21-22 and FIGS. 24-28. As shown, the article or single use tip, generally designated 200, consists of an elongated tip sleeve 202 composed of polycarbonate, an elongated forked tip member 204 composed of clear polycarbonate, and an overmold 206 composed of rubber or a thermoplastic elastomer. The single use tip 200 is mounted on nozzle 34, from which further extends lightpipe 30. Tip sleeve 202 is received onto nozzle 34, the rear end 210 being detachably attached to nozzle 34 by means of a bayonet joint consisting of peripherally extending arcuate ribs 96 coacting with slots 98, which can be seen in FIG. 12, and are further described in the associated description thereof. The tip sleeve is mounted to nozzle 34 to leave a small gap 201 between the end of the tip sleeve and the face of the instrument, as can be seen in FIG. 21. Tip sleeve 202 has a flange 205 at its rear end and is reinforced by ribs 203. Tip sleeve 202 is provided on its interior surface with a longitudinally extending frangible rib 86 that coacts with ramp 82 on nozzle 34 to close interlock 43, see FIGS. 12, 16 and 17 and relevant description supra.

Forked tip member 204 consists of a transparent cup 212 having a sidewall 222 and bottom wall 224 that is rounded exteriorly to form of a lens 214. A pair of prongs 216 is integrally formed with the sidewall of cup 212. The prongs 216 extend spaced apart forwardly and downwardly terminating in free ends 218. The angle of the longitudinal axis of the prongs relative to the longitudinal axis of the tip sleeve 202 is about 55 degrees. The space 220 between the two prongs 216 adjacent their free ends 218 defines the preselected injection site. Light emanating from the end of lightpipe 30 is directed by lens 214 generally toward the injection site. The inside of side wall 222 of cup 212 is tapered to engage the end of the lightpipe 30 in a tight manner. Lightpipe 30 is rotatably driven by a motor, mounted in instrument 10, via an eccentric cam 26, as can be seen in FIGS. 18-20.

Lightpipe 30 is held in nozzle 34 adjacent the forward end by an O-ring 230 constrained by a rib 232, and the forward end of the nozzle 34, that allows lightpipe 30 to vibrate freely. The O-ring 220 can be stuffed into a D-shaped groove formed in the interior surface at the end of the nozzle 34. The overmold 206 is rubber or a thermoplastic elastomer having a durometer of, for example, about 40 A but may vary from about 30 A to about 50 A. The overmold 206 extends from the free ends 218 of the prongs 216 to and over the forward end 240 of the tip sleeve 202, portion 206a of the overmold covers the end of the tip sleeve 202. The forward end 240 of the tip sleeve 202 is grooved on its exterior surface to provide alternate peripheral grooves 242 and ribs 244 that serve as a strong gripping surface. Overmold portion 206a covers and fills the grooves and the ribs.

Tip sleeve 202 is slightly spaced from the forked tip member 204 and the annular space between them is filled with overmold portion 206b. The spacing isolates the member 204 from the sleeve 202 and enables the forked tip member 204 to vibrate freely relative to the sleeve 202. Overmold 206 covers the exterior surface of the forked or pronged tip member 204, except for lens 214 of the cup 212. The entire surfaces of the prongs 216 are covered by overmold 206. The overmold 206 at the free ends 218 of prongs 216 is thicker and formed with a bulb shape 252. The overmold 206 at approximately halfway up the prongs 216 starting at point 254 up to the cup 212 is made wider on the inside of the prongs 216, as indicated by reference numeral 266, to provide surfaces 256 that can assist in retraction of skin or tissue. Each of these surfaces 256 is provided with a longitudinally extending groove 258 to assist in the removal of saliva or other liquids that may be present. In addition, the tip member is provided with one or more holes 270, advantageously not through holes, that have a bore of capillary size, so that saliva or other body liquids will become drawn into and trapped therein during use. This should additionally discourage attempts to re-sterilize a used tip, which may not be effective.

Figure 30:
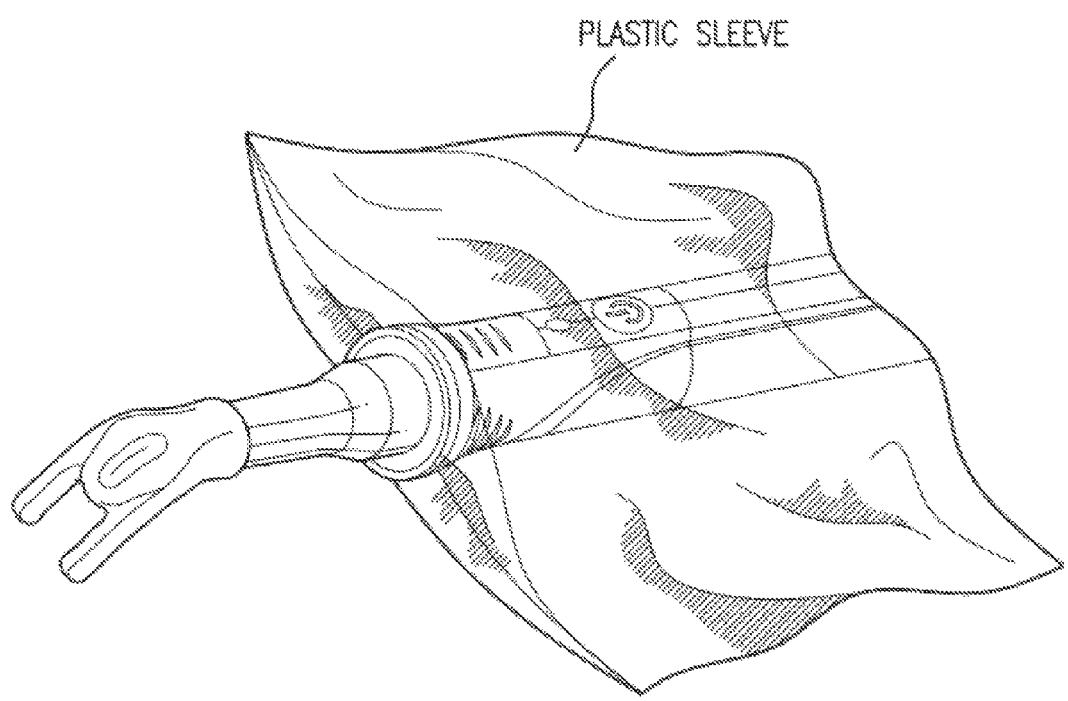
FIG. 30 shows a plastic wrapper mounted on an instrument to enable the dentist or doctor to use the instrument without affecting its sterility.

FIG. 30 shows how a plastic sleeve or wrapper can be placed around the instrument to protect its sterility and avoid contamination during use. The plastic sleeve or wrapper has a hole punched in it so it can fit over nozzle 34, and the disposable tip can be mounted over the nozzle 34 as described. To this end, the flange at the rear of the disposable tip is spaced slightly from the face of the instrument to provide a slot 201 to accommodate the plastic sleeve or wrapper in between the instrument and the tip, as illustrated in FIG. 21.

If the device or instrument is to be used for a medical application, that is, to some part of the body other than the mouth, the disposable tip can curve upwardly, 180 degrees opposite from the dental application described above, and the legs 216 of the tip member 204, or other tip member shape, can be uncoated by the overmold, with the overmold 260 bridging and holding together the cup of the tip member and the ribbed end of the tip sleeve, as shown in each of the drawings of FIG. 29. It should be apparent to one skilled in the art, from the above description that the present disclosure can be utilized in a variety of procedures requiring a skin or flesh puncture. Such other procedures include therapeutic inoculations, including shots to give patients medication, or to draw blood or fluids, and other potentially painful procedures. Such procedures can be performed on any portion of the body such as the arm, legs, buttocks, torso, etc.

Further in accordance with the disclosure, a noise generator can be mounted in the main body of the instrument so that the vibration is accompanied by a noise that will provide a distraction. In another embodiment, the noise generator cancels the noise of the vibration.

The tip is vibrated and has a free end characterized by a shape to induce vibrations in the tissue and underlying bone, whereby the free end can be placed in proximity to a preselected injection site on a human or animal and the tissue and underlying bone at said preselected injection site is vibrated while an injection is given. The vibrations are continued even after the injection has been completed to massage the tissue to dissipate the injected liquid into the tissue and prevent tissue distension and swelling of the tissue, which is a source of pain. Preferably, the subsequent vibration is effected with more pressure on the tissue by the person injecting to effect better massaging.

The subsequent vibration is most effective if the pressure applied is sufficient to sound bone beneath the tissue. An ordinarily skilled-in-the-art dentist can sense when he is applying pressure to tissue, such as the gums, and his instrument is effectively touching and in good contact or hitting on underlying bone. When such bone contact is sensed, the pressure is maintained for at least 1 up to about 30 seconds or until any tissue distension is no longer observed.

The disclosure provides an instrument for minimizing pain during administration by injection of a liquid, such as, an anesthetic, the instrument comprising a main body, a single use detachable tip, in some embodiments a cantilever mounted on the main body in a unique manner to prevent re-use of the tip, and a vibration unit mounted in the main body which, when initiated, causes the tip to vibrate. The vibrating tip can form a bifurcation of two spaced projections defining a space between them, whereby the spaced projections can be placed in proximity to a preselected injection site, for example on opposing sides of the site, on a human or animal, and the tissue at the preselected injection site can be vibrated while an injection is given to reduce the sensation of pain.

The vibration can be continued to massage the tissue to dissipate the injected liquid into the tissue, and to prevent or reduce distension and swelling of the tissue. The subsequent vibration can be effected with more pressure on the tissue by the person injecting to effect better massaging. The subsequent vibration is most effective if the pressure applied is sufficient to sound bone beneath the tissue.

An ordinarily skilled-in-the-art dentist can sense when he is applying pressure to tissue, such as the gums, and his instrument is touching the gums, or is in good contact or effectively hitting on underlying bone. When tissue or bone contact is sensed, the pressure can be maintained for 1 to 90 seconds. The area of the injection site is lighted by the instrument in a unique way. Also, performance is obtained by pulsing the vibrations according to a desired duty cycle, such about one second on and about $\frac{1}{10}$th of a second off.

An article, described with reference to the figures in greater detail below, has the form of a single use or disposable tip that includes a tip sleeve composed of a hard plastic such as polycarbonate, for mounting on the forward portion of an instrument by means of a detachable connection, such as a bayonet type connection, and a forked tip member, also composed of a hard plastic. These parts can be held together in a slightly spaced relation by an overmold of rubber or a thermoplastic elastomer having a preselected durometer. The forked tip member has a plastic cup formed in its base that is mounted on the vibrated lightpipe that projects out from the front of the instrument. A lens formed in the end of the cup shines light from the lightpipe onto the injection site. The prongs of the forked tip member extend forwardly and bend downwardly at an angle of approximately 55 degrees. An O-ring holds the lightpipe centered in the forward part of the instrument while allowing the lightpipe to vibrate freely.

The detachable tip includes a surface that can act as a retractor, and a control switch can be provided on the main body for on/off control of the vibration unit. Additionally, the tip can include an element that coacts with the instrument body so that when placed on the body, the element activates a switch or contacts to enable the instrument to be activated. In an embodiment, when the tip is removed by the necessary manipulation described herein, the overmold of rubber or a thermoplastic elastomer is torn sufficiently so that reuse of the tip is impossible. As in the previous instrument, the instrument can include a music player in the main body for playing music through a speaker. Further the main body can include rechargeable batteries as a power source to drive the vibration unit. Still further, a light source can be provided on the main body that is directed toward the space defined between the spaced projections, to light the area being injected to provide better visibility.

In accordance with the disclosure, a method of using the instrument includes vibrating tissue of a human or animal in a unique manner that maintains the vibration fresh and effective, and in proximity to a preselected injection site, while injecting by a needle or like instrument of a liquid is simultaneously carried out at the preselected injection site. The vibration can be continued, with more pressure applied to massage the injection site, to dissipate the injected liquid and to distribute the liquid into the surrounding tissue.

The instrument of the disclosure includes a main body having a forward end, a light-transmitting rod or lightpipe mounted in the body freely for vibration and projecting out of the forward end, a tip composed of a tip sleeve removably mounted on the forward end of the main body, and a tip member which can be pronged to define a forward bifurcation which can be aligned proximate a preselected injection site on a human or animal, the tip removably mounted on the lightpipe.

The tip sleeve and pronged tip member are covered and held together by an elastic overmold which allows light from the light rod to illuminate the injection site. A vibration unit is mounted in the main body and coupled to the light rod such that, when initiated, imparts vibrations via the light rod to the pronged tip member. The instrument can comprise means for controlling the vibration unit for an on-off duty cycle; the duty cycle can be about 1 second on and about $\frac{1}{10}$ second off. The pronged tip member may include at least one surface to act as a retractor. The tip sleeve and main body can include mutually coacting members to prevent reuse of the tip. The light rod can be composed of polycarbonate and the light rod is held by an O-ring at the forward end in order to be vibrated freely.

A music player may be included in the main body for playing music through a speaker.

In an embodiment, a pronged tip member comprises a cup and an integrally formed pair of longitudinally extending prongs, with the overmold of the prongs having a wider portion to provide at least one retraction surface, and on the underside, grooves to collect saliva. Due to this, it is important to ensure that the disposable tip is not reused. At least one longitudinal groove may be formed in the wider portion of the overmold. In an embodiment, the overmold at the ends of the prongs is bulbous. The forward end of the tip sleeve can define an alternate groove and rib, and the overmold can fill the groove and anchors in the rib.

Figure 31:
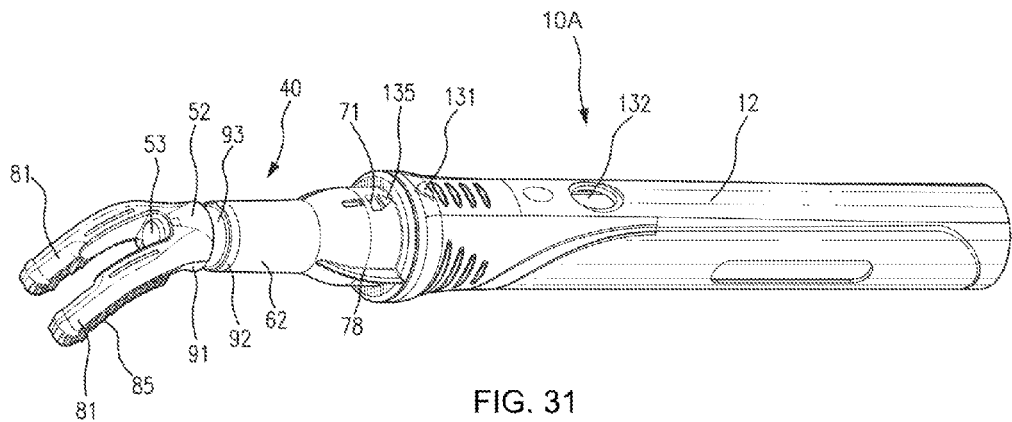
FIG. 31 is a perspective view of the novel instrument with a disposable tip mounted thereon.

In an alternative embodiment of the disclosure, and with reference to FIGS. 31-42, an instrument 10A is shown generally in FIG. 31. In this embodiment, like reference numerals perform a like function as described for other embodiments herein.

Figure 32:
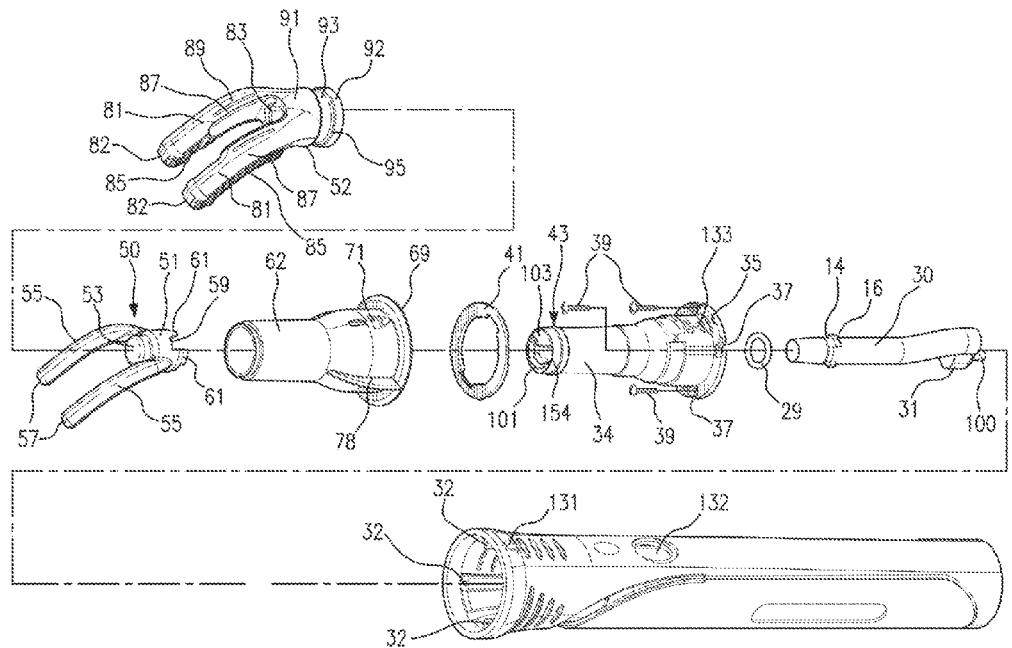
FIG. 32 is an exploded drawing showing an embodiment of the apparatus of the present disclosure with a disposable tip.
Figure 33:
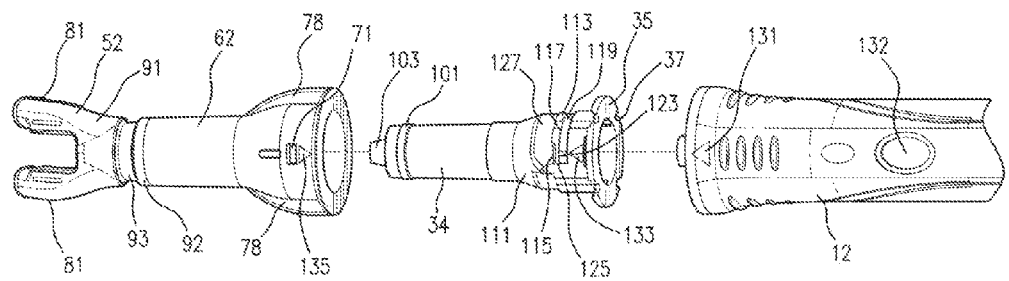
FIG. 33 shows in an exploded drawing how the removable or disposable tip is mounted on the end of the instrument.
Figure 34:
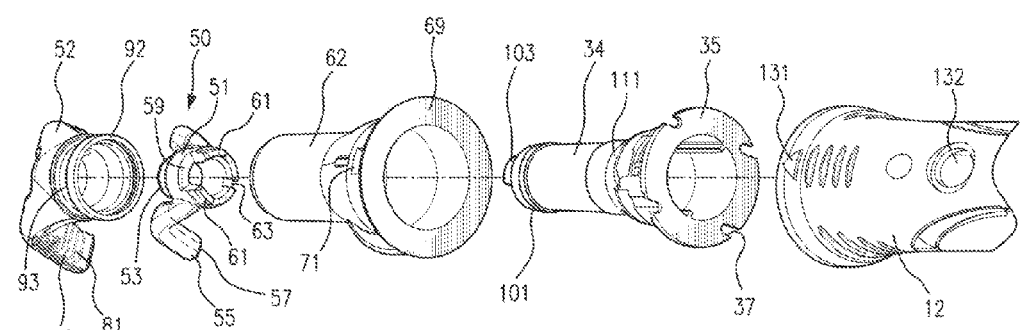
FIG. 34 shows in an exploded drawing in a different perspective the main components of the instrument.

With reference to FIG. 32, the forward end of the handle 12 is provided with 4 recessed bolt mountings 32. A handle sleeve 34 has a flange 35 at its rear end provided with 4 bolt openings 37 to receive bolts 39 to fix the handle sleeve 34 in a recessed position to the handle 12. A cover annulus 41 is fitted into the handle 12 to close the opening and cover the bolts 39. The light rod 30 passes through the handle sleeve 34 and projects outwardly from it. The O-ring 29 resiliently engages the inner surface of the handle sleeve 34 near its forward end. The front end of the handle sleeve 34 has a low flange 43 set back from the open front end.

Each component of the disposable tip 40 will now be described in more detail. The plastic tip 50 consists of a cup 51 with its closed end defining a lens 53. Two curved protrusions or legs 55 extend from the sides of the cup 51 bracketing the lens 53, extending forwardly and terminating in free ends 57 that are rounded. On its rear facing side, the cup 51 has a cutout 59 and two tongues, tabs or positive ribs 61 that extending rearward, one on each side of the cutout 59. Diametrically opposite cutout 59 is a small cutout 63. The rod 30 enters into the cup 51 and firmly and rigidly engages the cup 51 and the forward end of the rod 30 is juxtaposed closely to the lens 53.

Figure 35:
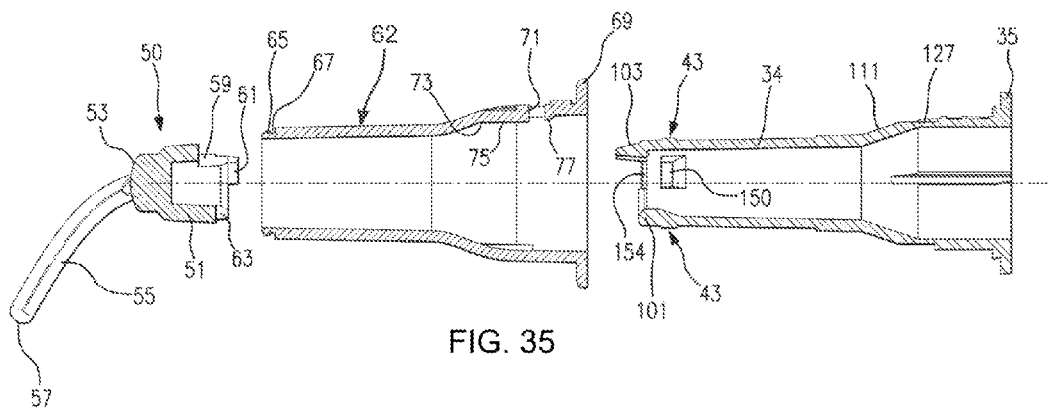
FIG. 35 shows in an exploded drawing in section the handle sleeve, the tip sleeve and the plastic tip of the instrument.
Figure 36:
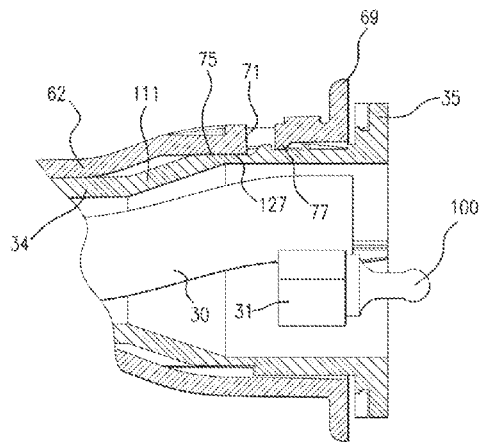
FIG. 36 shows in section the rear portion of the assembly view of FIG. 7 showing the position of the light rod of the instrument.
Figure 38:
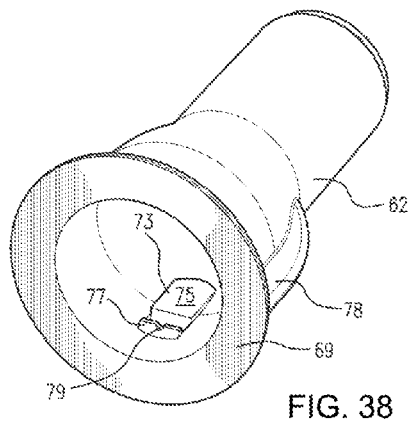
FIG. 38 is a perspective view showing the tip sleeve.
Figure 37:
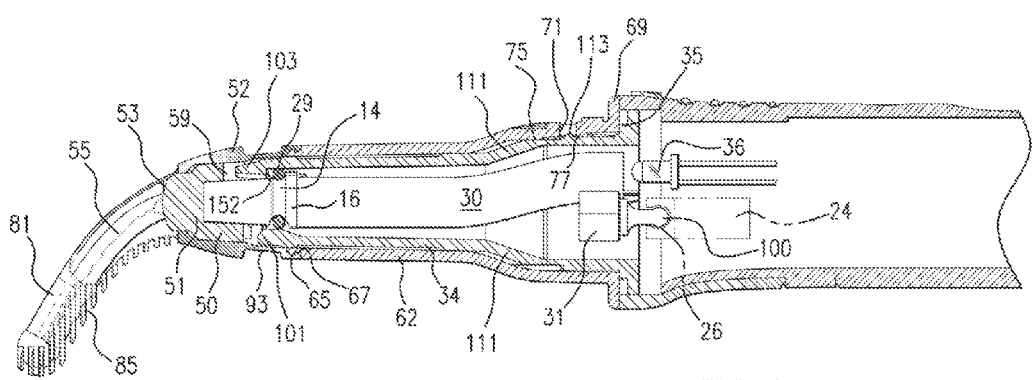
FIG. 37 is an assembly view in section of the disposable tip mounted on the handle sleeve of the instrument.
Figure 39:
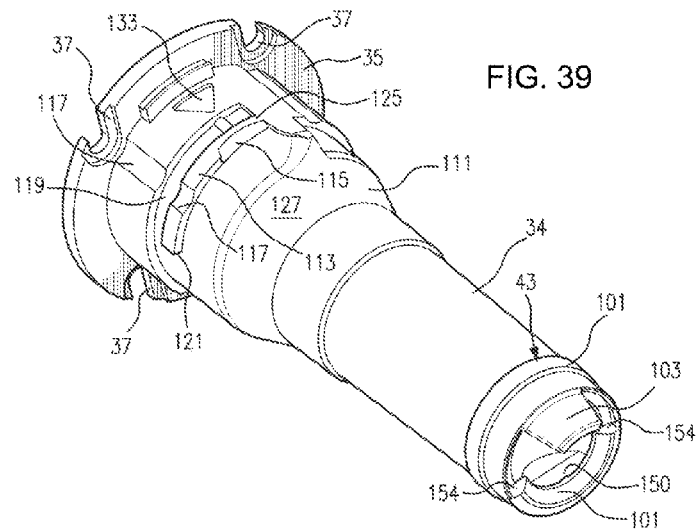
FIG. 39 is a perspective view showing the handle sleeve.

The tip sleeve 62, as can be seen in FIG. 35, consists of a tube having at its forward end a ridge 65 and behind it a groove 67. At its rear end, tip sleeve 62 increases in diameter conically and terminates in a flange 69. Adjacent its rear end, a rectangular through opening 71 is formed in the shell of the tip sleeve 62. On the forward side of the opening 71 the inside of the tip sleeve 62 is thickened at 73 to form a flat shelf 75 that is generally the circumferential width of the opening 71. On the rear side of the opening 71 the inside of the tip sleeve is thickened to form an inwardly extending plate 77 also generally the circumferential width of the opening 71. Plate 77 has a v-notch 79, visible in FIG. 38, formed at its inmost extent. Reinforcing ribs 78 are positioned on the exterior of the tip sleeve 62, extending from the conical section to the flange 69.

Figure 7:
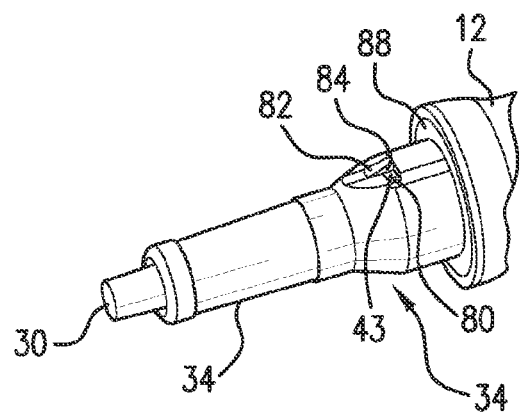
FIG. 7 shows in perspective a rotated view of the end of the instrument.

Overmold 52 is hollow and the forward portion has two longitudinally extending arms 81 that fit over the longitudinally extending legs 55. The free ends of the arms terminate in an enlarged end bulbous portion 82. The overmold 52 is composed of rubber or a thermoplastic elastomer having a durometer of preferably about 40 A but may vary from about 30 A to about 50 A. Portion 91 of the overmold fits over the cup 51 and has a hole 83 that fits around the lens 53 to let the light shine through. The two arms 81 have a series of transversely extending, longitudinally spaced grooves 85 on the underside, defined by projecting filaments, to trap saliva so reuse of the disposable tip will not be attempted. The two arms 81 of the overmold 52 can be smooth or have many filaments in the form of ribs as shown in FIG. 7, or an array of projecting filaments of any shape, projecting off of the surface of the overmold arms 81, providing a greater stimulation to the tissue while in use. An intermediate portion 87 is enlarged transversely on both arms 81 of the overmold 52 to collectively form a retractor surface 89 to help press away or retract tissue. Rear portion 92 of the overmold 52 has a reduced thinned section 93 that at the rear is integral with a terminal section 95 complementary in configuration to the forward end of the tip sleeve 62 to fit over the ridge 65 and behind it in the groove 67 to anchor the overmold 52 to the tip sleeve 62 and holds it spaced from the tip 50.

Figure 12:
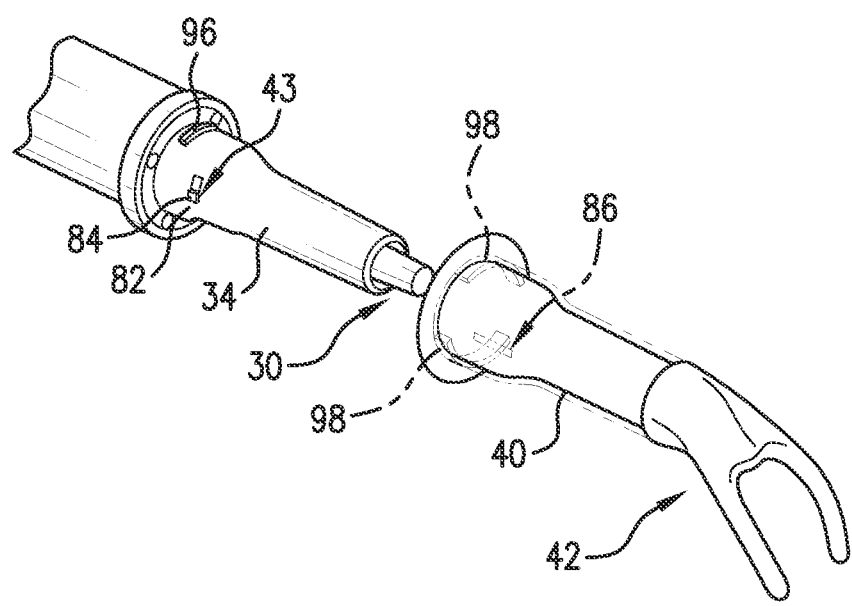
FIG. 12 shows in perspective a partially exploded view showing the tip removed from the nozzle of the instrument.
Figures 40, 41, 42:
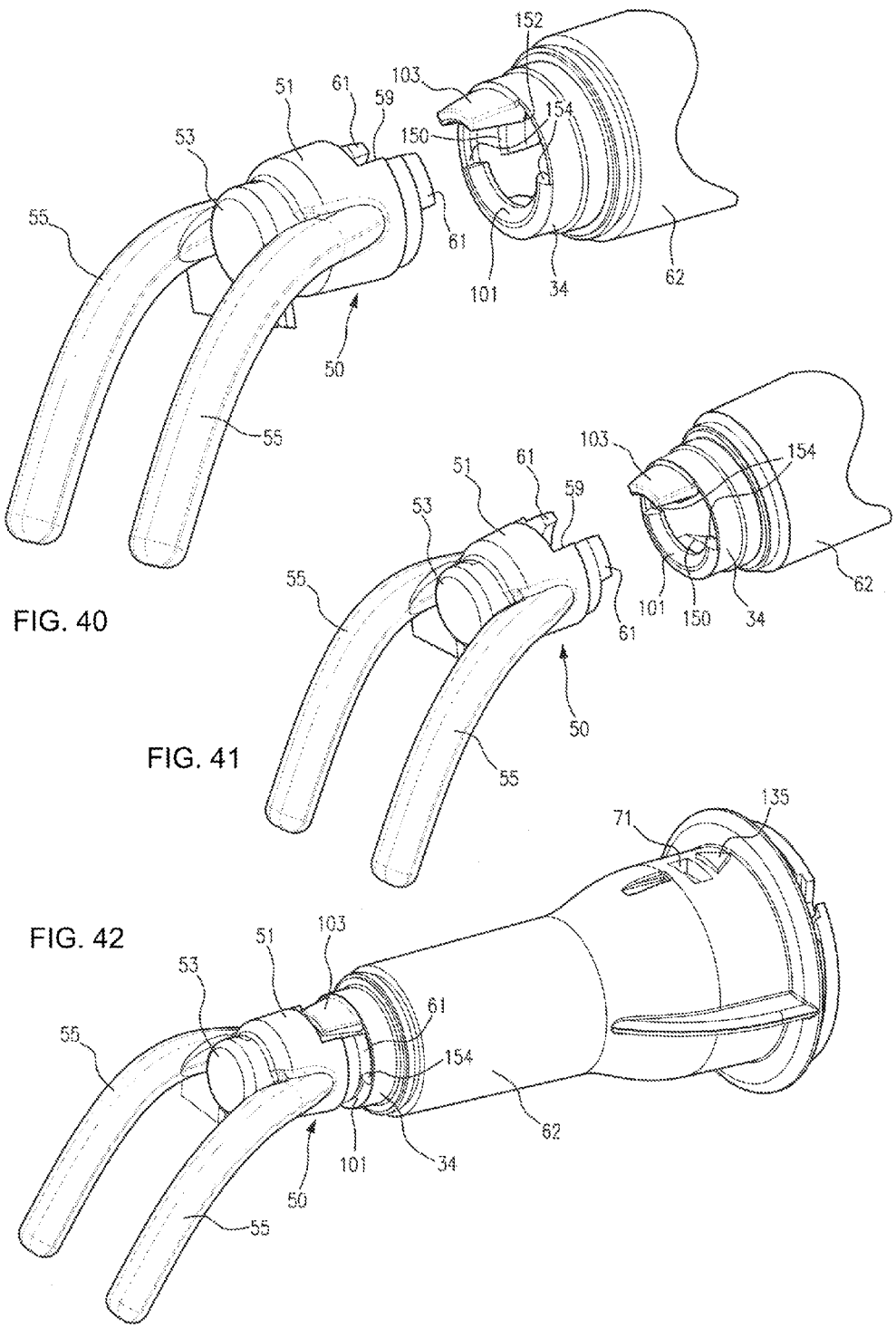
FIG. 40 is an exploded view in perspective showing the tip mounting to the instrument sleeve.
FIG. 41 is a similar exploded view in perspective showing the tip just before mounting on the instrument sleeve.
FIG. 42 is an assembly view in perspective showing the tip mounted on the instrument sleeve.

Handle sleeve 34 is a longitudinally extending tube and has at its forward end, a circumferential radially inward flange 101 that terminates spaced from either side of a tapered protrusion or tooth 103 extending axially or longitudinally forward level with the forward end of the sleeve 34, to define recesses 154, see particularly FIGS. 40-42. The tooth 103 extends slightly into the sleeve 34 forming a rear shoulder 152. Circumferential flange 101 formed at the forward end of the handle sleeve 34 serves as a constraint on the forward side to hold the O-ring 29. O-Ring 29 also passes behind and bears on shoulder 152 of tooth 103 and thus, is constrained on the forward side also by the tooth 103. These elements together hold the light rod 30 on the forward side in position within the forward end of handle sleeve 34. On the rear side, projection 16 on the light rod is constrained by arcuate radially inwardly projections 150 one of which is seen in FIGS. 10 to 12. Also seen in FIGS. 40 to 42 are recesses 154 formed on either side of the tooth 103 between the terminating ends of the circumferential flange 101 and the tooth 103. Recesses 154 are about 1-2 mm deep. As noted, only the O-ring 29 engages the inner surrounding surface of handle tip 34. The rod 30 with the O-ring 29 acting as a pivot is otherwise completely free to vibrate.

The handle sleeve 34 at its rear end is of larger diameter with a transition conical section 111 between the front end and rear end. The rear end terminates in flange 35 having bolt opening 37. Spaced forward of the flange 35 is a surface portion 127 of the conical section 111 that is of fixed diameter. An arcuate ridge 113 is formed that extends circumferentially from a point 125 of larger diameter than portion 127 circumferentially for about 60 to 90 degrees and terminates at point 121. Ridge 113 is narrowed by cutout 115 on its right side as viewed in FIG. 39 and has a dip 117 to enable a bolt to pass through to a screw or bolt opening 37.

The ridge 113 defines a groove 119 on its rear side, due to surface 127 having a fixed diameter and a low rib 123 extends longitudinally in groove 119 to the rear of cutout 115.

Each of tip sleeve 62, handle sleeve 34 and handle 12 can have indicia to show how the parts are intended to line up. Handle 12 has an arrowhead 131 pointing forward on its front end aligned with the control button 132 to turn the power on and off. Handle sleeve 34 has an arrowhead 133 pointing forward just behind the flange 35. The disposable tip 40 has an arrowhead 135 on tip sleeve 62 pointing rearward so that when the disposable tip 40 is pushed longitudinally onto the handle sleeve, the tooth 103 will be inserted or protrude into the cutout 59 of the plastic tip 50, but with clearance from both the plastic tip 50 and light rod 30 so that vibration of tip 50 by light rod 30 is not interfered with in any way. Also, the rear ends of positive ribs 61 will be received and positioned in recesses 154 in the handle sleeve 34, but with clearance from the handle sleeve 34 and tooth 103 so that tip 50 vibration is not interfered with in any way. The positive ribs 61 of tip 50 and recesses 154 of handle sleeve 34 are complementary and the clearance between them is at least about 0.5 mm. See particularly FIGS. 40-42.

As the disposable tip 40 is being pushed onto the handle sleeve 34 in a linear longitudinal direction, the thickened area at 73 that forms a flat shelf 75 causes the inwardly extending plate 77 to ride over the ridge 113 at cutout 115 and to pass behind into the groove 119, whereupon the flat shelf 75 drops down onto the surface 127, the rectangular through opening 71 straddles the ridge 113 at the cutout 115 and the plate 77 drops onto the rib 123 with the v-notch 93 engaging the rib 123. At this point, the rod 30 is received in and positioned in the cup 51 of the tip 50 of the disposable tip 40, which is latched onto the handle sleeve 34 and cannot be pulled off axially. The tooth 103 at the forward end of handle sleeve 34 is received in and positioned in the cutout 59 with suitable clearance all-around of at least about 0.5 mm so that there is not any interference respecting vibration. Also, the rear ends of the positive ribs 61 on either side of the cutout 59 are received in the recesses 154 to a sufficient depth to enable back-up engagement with the handle sleeve 34 in the event there is any relative rotary motion with respect to the handle sleeve 34 and the tip 50. Both the tooth 103 and the rear ends of the positive ribs 61 serve to hold the handle sleeve 34 and the tip 50 from relatively rotating. The tooth 103 and the positive ribs 61 will, at this time, be juxtaposed in the same radial cylinder coaxial with the longitudinal axis of the instrument, the handle sleeve 34 and the cutout and the tabs 61 of cup 50.

To remove the disposable tip 40 from the handle sleeve 34, it is necessary for the tip sleeve 62 to be rotated relative to the handle sleeve 34 from adjacent point 125 toward the terminal point 121 until the plate 77 clears this point 121, at which time, the disposable tip 40 can be removed by longitudinally pulling forward. However, during the relative rotary motion between the tip sleeve 62 and handle sleeve 34, the plastic tip 50 will quickly engage the tooth 103, either by the side walls of the cutout 59 or the tabs or positive ribs 61 or both and the tip 50 will then be held stationary and prevented from rotating. The tip sleeve 62 will still be rotatable relative to the handle sleeve 34 so it can be removed, and in this process as the tip sleeve 62 is rotated, a torsion force will develop and be imparted to the overmold 52 and the elastic limit of the overmold 52 at the thinned section 93 will quickly be exceeded and the overmold will experience a severe tearing or shredding of the thinned section 93 of overmold 52 over about 60 to 90 degrees or more destroying effectively its utility and/or its ability to be reused. The rear end of the positive ribs 61 of tip 50 being in the recesses 154 is a back-up in case of any failure of the tooth 103 to hold the tip 50 stationary during demounting of the disposable tip 40 from the sleeve 34. The rear ends of the positive ribs 61 being positioned in recesses 154 will also prevent any rotation of tip 50 relative to handle sleeve 34 during the demounting of disposable tip 40 and thereby ensure the tearing or shredding of the thinned section 93 of overmold 52.

In embodiments of the disclosure, overmold 206 is not torn. More particularly, in certain applications, for example for home use in reducing pain during blood sampling or injections, the risks of reuse may be reduced, and limited reuse as otherwise provided for herein, for example as shown and described with respect to FIGS. 45-55, is acceptable. Further, in some applications, it may be desirable to replace tip 40B, for example to use a different shape or size tip 40B, for example for different applications or patients, while still enabling limited reuse of removed tips. In these embodiments, elements which prevent removal without destruction can be eliminated.

For example, in the embodiment of FIG. 12, vertical surface 84 is removed, and rib 86 can reversibly engage electrodes 45. Similarly, in the embodiment of FIG. 32, tooth 103 and ribs 61 can be eliminated, allowing distal tip 50 to rotate together with tip sleeve 62, to be removed together therewith without tearing overmold 206. In these embodiments, overmold 206 can be eliminated entirely, and tip 50 can be connected to tip sleeve 62 in any manner which permits vibration of tip 50 in the manner provided in other embodiments. For example a flexible sleeve can be used to connect tip 50 and tip sleeve 62. It should be understood that overmold 206 can still provide other benefits, however, including ease of cleaning, and a more attractive appearance.

In embodiments where overmold 206 is eliminated, distal tip 50 must be connected to a base remainder of 40, or base 44, in FIGS. 51-57. In an embodiment, distal tip 50 is molded together with tip sleeve 40. In another embodiment, distal tip 50 is removable from base 44, as shown in FIG. 55. This embodiment, tip 40B is shown in FIGS. 51-55, for example. A narrowed and thinner region 93A of molding can be formed to enable greater vibration of distal tip 50 relative to base 44, although this is not required in all applications. Tip 40B, in particular, can be produced with overmold 206 and tooth 103, combining the RFID usage control aspects, or tip 40B can be produced without overmold 206, as described herein.

As described, the fitting member 31 attached to the end of the light rod 30 includes a projecting stub with ball end 100 as a cam follower for contacting and following the cam 26 to impart the vibratory motion of the cam 26 to the light rod 30. The end of the light rod 30 is in alignment with the LED 36 as previously described. As described elsewhere herein, although continuous pulsing can be used, it has been discovered that a pulsed vibration sequence can be more effective. A pulsed sequence of about one second on and then about a tenth of a second off, is sufficient to pulse the vibration without allowing the vibration of the tip to ever drop down to zero. In this manner, the device or instrument pulses about every second, re-stimulating the nerves in the area. To this end the electronics controlling the pulsing is modified to include the necessary means for pulsing and obtaining the desired on/off duty cycle as noted. The motor is energized using 110 volt AC (50-300 Hz frequency). The frequency can vary from about 50 Hz to about 300 Hz with about 140 Hz to 160 Hz being preferred. The vibration at the free ends of the prongs or forks 42 can vary from about 0.1 mm to about 1.0 mm, in an embodiment advantageously 0.65 mm to 1.0 mm, with a duty cycle of about 1.05 seconds with on pulsing of about 1 sec. and off of about 0.05 sec. The vibration amplitude may vary from about 0.1 mm to about 1.0 mm, with the preferred range being from about 0.0.65 mm to about 1.0 mm. Depending on a patient's physiology, a larger or smaller amplitude than specified can be more effective.

The novel instrument 10A exhibits enhanced amplitude and percusses the tissue contacted, and causes a deep penetration of the vibratory stimulus into the oral mucosa of a dental patient, for example, thereby stimulating the nerve receptors, for example A-beta nerve receptors, which are located deep within the tissue, thereby stimulating the sensory nerve receptors located deep within the tissue, creating action potentials which send sensory information to the brain via myelinated A-beta afferent nerve fiber axons.

Additionally, vibration is sent out in a full 360 degrees around the disposable tip 40, mainly, from three places off of the tip, namely, from each free end of the curved downwardly arms, as well as, from the paddle or retractor portion 87. Also the joint with tip sleeve 62 at times will stimulate the lip or cheek or bone when resting against it. The enhanced vibration is not limited to just the area at the ends of the curved downward arms. Alternative tip free end shapes are shown in WO/2010/111611.

A plastic sleeve or wrapper can be placed around the instrument to protect its sterility and avoid contamination during use. The plastic sleeve or wrapper has a hole punched in it so it can fit over the handle sleeve 34, and the disposable tip 40 can be mounted over the handle sleeve 34 as described. To this end, the flange at the rear of the disposable tip 40 is spaced slightly from the face of the instrument to provide a slot to accommodate the plastic sleeve or wrapper in between the instrument and the tip.

If the device or instrument is to be used for a medical application, that is, to some part of the body other than the mouth, the disposable tip 40 can curve upwardly, 180 degrees opposite from the dental application described above, and the legs of the tip member 50, or other tip member shape, can be coated or uncoated by the overmold with the overmold 260 bridging and holding together the cup of the tip member and the ribbed end of the tip sleeve 62.

The vibration provided by instrument 10, 10A can be particularly effective if transmitted to a cylindrical volume of tissue and underlying bone at the injection site, and particularly on opposite sides of or surrounding the injection site.

Figure 43:
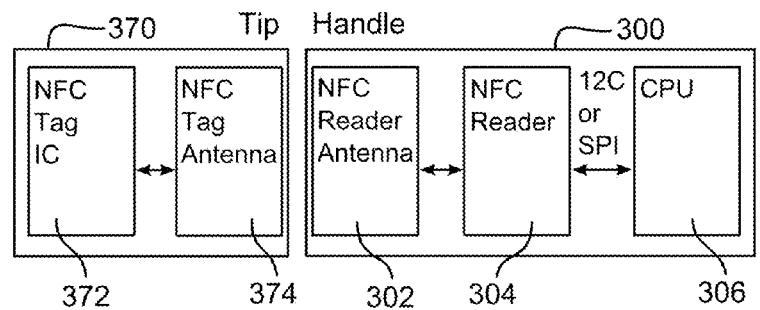
FIG. 43 is a schematic view of communication between a tip and reader of the disclosure.
Figure 44:
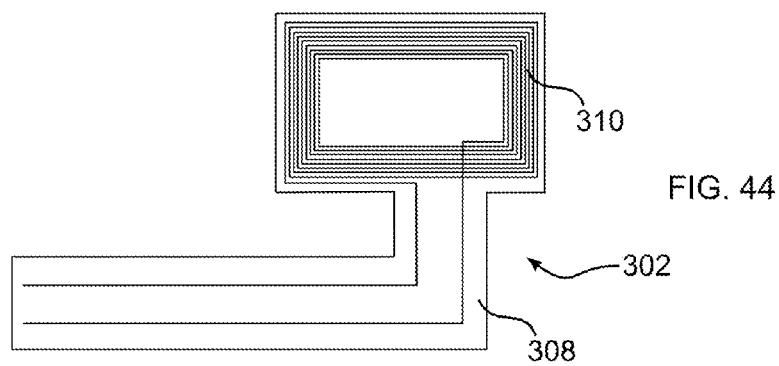
FIG. 44 is a diagram of a reader antenna of the disclosure.
Figure 45:
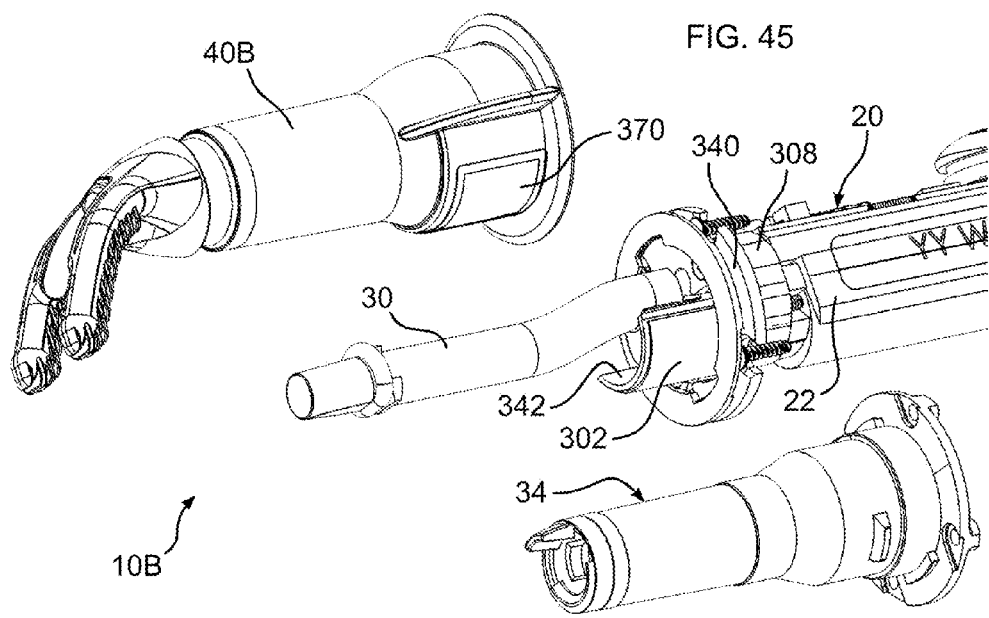
FIG. 45 is an exploded perspective view of an end of an instrument of the disclosure, with the tip and nozzle removed, showing tag and reader antennas.

Referring now to FIGS. 43-45, an electromagnetic radio frequency transmitter/receiver, or reader 300 associated with handle 12 communicates with a radio frequency tag 370 associated with disposable tip 40B. Although a variety of tag types can be used with the disclosure, as described further herein, tag 370 includes an antenna 374, and typically a simple processor 372. To reduce component requirements, and to keep the cost of disposable tip 40B low, it is advantageous for tag 370 to be of the passive type, which receives energy from a received wave signal sufficient for the tag to transmit information using antenna 374. Accordingly, for a passive tag, an energy source does not need to be provided within tip 40B and connected to tag 370. Conversely, an active tag 370 would include an energy source, such as a battery (not shown).

Reader 300 includes a reader antenna 302, reader integrated circuit (IC) 304, and reader CPU 306. Reader IC 304 functions to carry out the communication protocol selected, for example ISO/IEC 14443A operating at 13.56 MHz, which is Near Field Communication (NFC) protocol, or any other protocol known or hereinafter developed, which is suitable for the short range, low cost and complexity, and low power requirements of the disclosure.

Accordingly, a near field protocol is advantageous. Reader IC 304 can have the form, for example, of TEXAS INSTRUMENTS part TRF7970ARHBR, which uses the Serial Peripheral Interface Bus (SPI) to transfer data, although other interfaces can be used. It should be understood that other types of electronic processors or CPUs can be used.

A longer distance protocol can be used, but may potentially increase the possibility of reading tags 370 that are not mounted to instrument 10. In an embodiment, however, a longer distance protocol is used, such as RFID for example, and tags can be distinguished by any of a variety of means including jamming, shielding, time based protocols, reading previously written contents, or any other known or hereinafter developed method.

A contactless communication technology is advantageous as no electrical connection must be manually created when adding tips 40B. As instrument 10 is used in a wide variety of environments, including a health environment, it is important that surfaces of instrument 10 are smooth and easily cleaned, and that surfaces that can trap contaminants, such as electrical contacts, are avoided. Additionally, a contactless connection can be more reliably established.

Tag 370 is configured or selected to be compatible with the type of Reader IC selected, and the protocol used. Tag 370 can have a clear substrate, wherein the antenna leads 310 are visible, or a white or other color substrate, which facilitate printing of visible indicia. In an embodiment, tag 370 is 18 by 12 mm, but can be other sizes, provided that it can be positioned within or upon tip 40B, and can further be oriented to lie close to reader antenna 302 when tip 40B is mounted upon handle 12. In one embodiment, tag 370 has a range of 5 to 8 mm, although longer or shorter ranges are useable. An example of a suitable tag is NXP NTAG 213 IC. This tag is configured to support security features useable to detect fraudulent tags or other abuse.

Security features can include one or more codes stored within tag 370 that are useable to validate an authenticity of the tag. Authenticity can mean that the tip has not been reproduced without authorization from the original manufacturer of the tip. For example, validation can include processing one or more codes stored in the tag, wherein the one or more codes can be processed to produce a result which is known only by the manufacturer of original tips. This processing can be performed by reader 300, possibly including reader CPU 306, another electronic processor or CPU within instrument 10B, or can be processed by an external processor not associated with instrument 10. In a further embodiment, tag 370 keeps a count of the number of times it has responded to a read request, or interacted with a NFC device. Additionally or alternatively, reader 300 or tag 40B can store a number of times that vibration has been applied to tip 40B, or can keep a count of the total amount of time that vibration has been applied to tip 40B. A hash tag algorithm can be carried out by a processor within instrument 40B, wherein an RFID readable code or number encoded within tag 370 is analyzed to determine if the associated tip 40B is authentic.

Reader CPU 306 is selected to process the data received from reader 300, including, for example, analyzing the data to determine the number of times tip 40B has been used, or a time period of use of tip 40B, and to determine if tip 40B has been tampered with. In an embodiment, for example, CPU 306 can designate a tip 40B as 'USED' when any of the following conditions are met: instrument 10B has been turned on 6 times; or the cumulative time instrument 10B has been 'on' exceeds 4 minutes and 45 seconds. The criteria can be changed for greater or fewer uses, or a longer or shorter cumulative 'on' time, or any other parameters suitable for the intended use or desired.

FIG. 48 illustrates one example embodiment of operation of instrument 10B. Software executing upon reader CPU 306, and/or another electronic processor or CPU within instrument 10B, carries out the following steps. Communication between reader 300 and tag 370 is established (400), it is determined if tip 40B is present (402), and whether the tip has been used beyond a predetermined number of times (406). Other criteria may also be evaluated, and if all parameters are acceptable, communication may be terminated (408), and instrument 10B can be operated (410). During operation, the number of times vibration has been activated is recorded (412), if this is an operating parameter to be monitored. When use has been concluded and instrument 10B is turned off, communication can be restarted (414), and the captured data can be written (416) to storage within tag 370. In some embodiments, the written data is encrypted. If usage criteria has been met or exceeded (418), the information written to tag 370 can include data indicating a 'used' state (420), wherein instrument 10B will not use that particular tip in a subsequent use, once this attribute has been read. Data pertaining to usage can, in an alternative embodiment, be written to data storage within instrument 10B, or can be communicated to a computing device external to instrument 10B.

One form of tampering of tip 40B could include creating a copy of tag 370 and replacing tag 370 within tip 40B. However, as described elsewhere herein, and as tag 370 is disposed within the interior of tip 40B, instrument 10B can include features which tear tip 40B when removed, thereby preventing replacement of tag 370. In addition, the tag architecture can include data which enables authentication of the tag, the data not being readable or decryptable. For example, a unique value can be stored into each tag 370 which can be analyzed by a processor within instrument 10B to determine if tag 370 is authentic. Additionally, tag 370 with antenna 374 can be permanently attached to tip 40B, whereby either or both of tip 40B and antenna 374 become unusably damaged if removal of tag 370 is attempted.

Reader CPU 306 can further be configured to communicate a status to a user of instrument 10, by activating any or all of lights (FIG. 47, 404), sound, a display screen, or another device by wireless communication. Additionally, reader CPU 306 executes software configured for implementing the communication protocol, for example an NFC protocol. In an example embodiment, reader CPU 306 includes a TEXAS INSTRUMENTS MSP430F5152IRSBR.

With reference to FIGS. 44-47, reader antenna 302 is configured to extend within tip 40B in order to be in close overlapping proximity to tag antenna 374, when a tip 40B is installed upon instrument 10. A mounting plate 340 is connected to chassis 22 and/or motor 24, to be positioned at a peripheral end of handle 12, past circuit board 20. Mounting plate 340 forms an attachment point for nozzle 34, and additionally provides a reinforcing backplate 342 for reader antenna 302.

With further reference to FIGS. 44-47, reader antenna 302 has a narrowed connector portion 308, which forms a right angle and includes an elongated portion. When installed within instrument 10B, connector portion 308 is passed through a slot 344 in mounting plate 340, and is then curved to extend to, and form an electrical contact with, circuit board 20. Nozzle 34 is positioned over reader antenna 302 and light rod 30, providing protection from mechanical damage to these components, while forming a guide and attachment points for tip 40B. In an example embodiment, the antenna wire portion of reader antenna 302 has a size of between 10×15 mm and 12×18 mm, although it should be understood that various sizes substantially smaller or larger can be used, depending on space within tip 40B, the communication protocol used, and the intended application for instrument 10B.

Figures 49, 50:
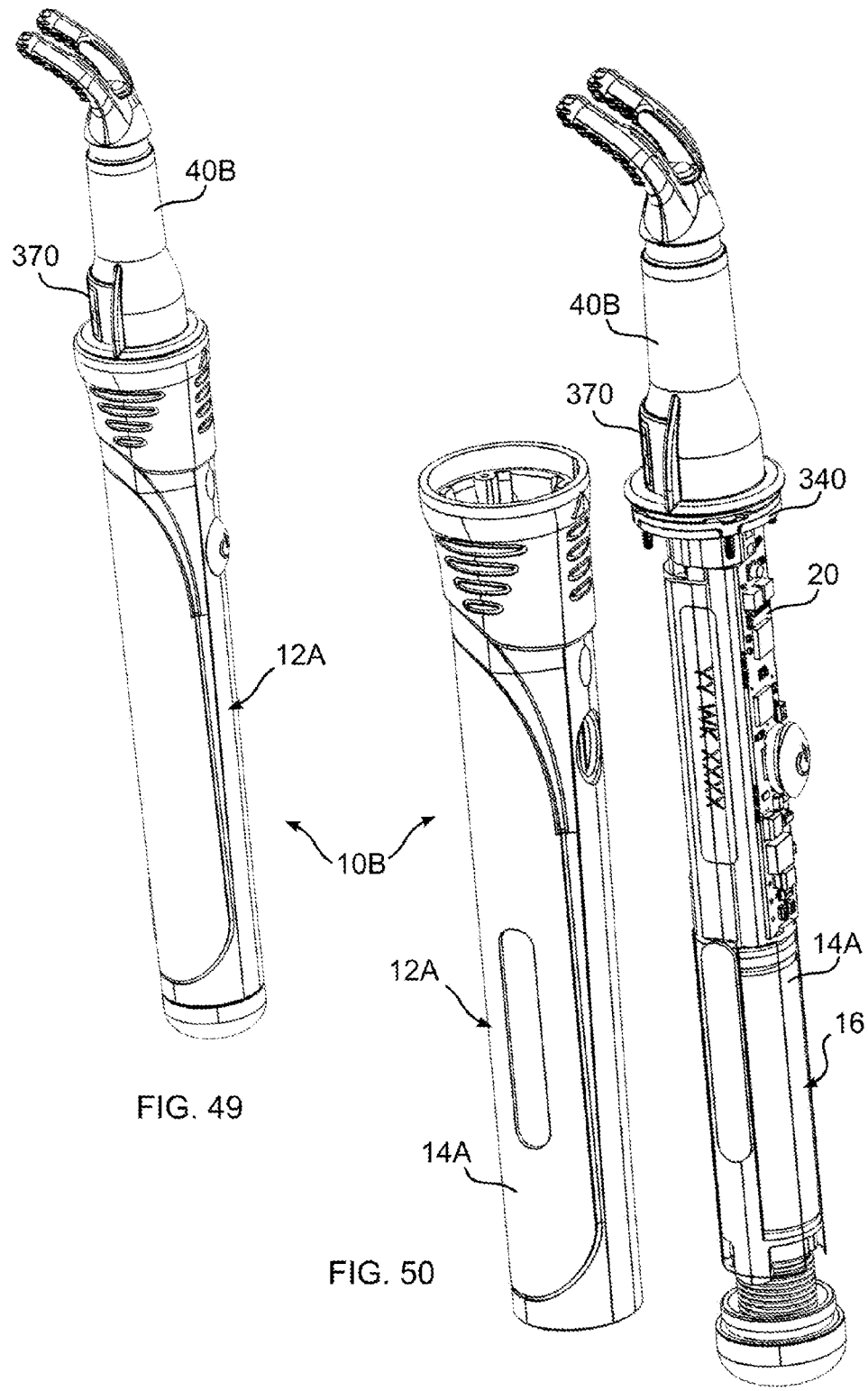
FIG. 49 is a perspective view of an instrument of the disclosure.
FIG. 50 depicts the instrument of FIG. 49, with a cover removed.

FIGS. 49-50 depict device 10B, including an alternative housing 12A of the disclosure, having a battery cover portion 14A.

In accordance with the disclosure, to reduce the size of the tag and reader antennas 370, 302, the antennas are partially or completely overlapping when tip 40B is installed upon nozzle 34, and during use. In an embodiment, the planar surfaces of the tags are spaced between 6 and 8 mm apart, although substantially closer or farther distances can be used, based upon space available, the strength of the sent and received signals, and the frequency employed.

With reference to FIGS. 51-55, an embodiment of tip 40B which does not include overmold 206 is illustrated, although other embodiments described herein can be used in the illustrated application, including devices 10 and 10B. More particularly, frame tip or distal tip 50 includes two longitudinally extending arms 81 which form a V-shape. This shape enables any narrow body part, including for example a tendon, toe, thumb, muscle, ear, nose, cheek, tongue or other mouth part, brow, or finger 500, to be inserted between the arms 81 of the V until contacted on opposite sides of the body part. In this manner, and as may be seen in FIG. 52, a single size of distal tip 50 can accommodate a range of sizes and parts. Additionally, distal tip 50 can be provided in a variety of sizes and shapes.

Further, as shown in FIGS. 54 and 55, arms 81 can be disposed at various angles with respect to handle 12. This angle can be selected to enable handle 12 to be positioned at a comfortable distance from the body when arms 81 are applied to the body. The angle can further be selected to foster a comfortable posture of the practitioner or patient when holding handle 12 when positioning a particular body part within arms 81. In the example of FIG. 54, and angle of 60 degrees is illustrated, and the example of FIG. 55, an angle of 45 degrees is illustrated. It should be understood that this angle can any angle. FIG. 55 further illustrates that tip 40B can be produced in separable components, although it should be understood that tip 40B can also be produced as a unitary part including base 44 and tip 50.

Once distal tip 50 contacts the body part which is expected to experience pain or discomfort, vibration can be initiated and continued as described herein. As described herein, this vibration can be at any of a range of frequencies, or along a range of frequencies, and a particular frequency or range of frequencies can be programmed or provided which best demonstrates efficacy with a particular body part, and/or a body part with particular characteristics, for example relating to skin thickness or sensitivity. As further described herein, the vibration can be pulsed or discontinuous.

Without being bound to any particular theory, as nerves proximate skin contacted by vibrating arms 81 are stimulated, nerve conduction associated with pain or discomfort is diminished. At this point, skin between or adjacent arms 81 can be pierced, abraded, treated with a chemical or medicament, or otherwise disturbed in a manner which tends to produce pain or discomfort. Vibration can be discontinued after an amount of time has passed whereby an initially high level of pain or discomfort would normally be expected to be sufficiently abated.

With reference to FIG. 56, it may be seen that distal tip 50A is provided with a lateral arm 81A which forms a closed loop between arms 81. In this manner, an inserted body part, such as finger 500 in FIG. 58, can be contacted at multiple points surrounding a site of pain or discomfort. Further, a loop can be used to retain the body part in contact with the vibration, which can be helpful for fearful or movement prone patients. Lateral arm 81A can also be provided with a gap, as shown in FIG. 57, which can enable arms 81A to bend to accommodate larger body parts, or to more resiliently contact the body part on opposing sides.

In FIG. 58, instrument 10B is shown applied to a finger 500, which is about to be pierced by lance 510, in order to obtaining a blood sample for a therapeutic application, such as glucose monitoring. It may be seen that finger 500 is inserted within distal tip 50A, although any other tip of the disclosure which can accommodate a finger can be used. In this example, finger 500 is pressed into the narrow portion of the V shape to increase contact with distal tip 50A, to better convey vibration to the skin of finger 500. Vibration is applied to the finger at intervals and frequencies described elsewhere herein, and the finger is lanced with reduced discomfort and pain, after which vibration can be terminated, and the finger 500 removed from distal tip 50A.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A device for vibrating body tissue, comprising:
   a frame;
   an activatable source of vibration positioned in the frame;
   a removable tip connectable to the frame and having a distal end, the tip connected to the source of vibration when the tip is connected to the frame to thereby vibrate the distal end when the source of vibration is activated;
   an electromagnetic reader positioned in the frame and including a first antenna configured to receive electromagnetic radiation; and
   an electromagnetic tag affixed to the removable tip and including a second antenna configured to send electromagnetic radiation in communication with the first antenna, the first and second antennas disposed proximate to each other with the first antenna overlapping an interior space of the tip when the removable tip is connected to the frame, the electromagnetic tag thereby configured to transmit information to the electromagnetic reader, wherein the first antenna of the electromagnetic reader receives information from the electromagnetic tag only when the first antenna overlaps the interior space of the tip or the first and second antenna are located a distance less than 8 mm apart.

2. The device of claim 1, further including a processor communicatively connected to the electromagnetic reader, the processor configured to execute software stored on non-transitory media, the software configured to store and process information provided by the electromagnetic reader obtained from the electromagnetic tag.

3. The device of claim 2, wherein processing information includes at least one of:
   (a) a count of a number of times that the source of vibration has been activated with a unique removable tip connected to the frame;
   (b) an amount of time that the source of vibration has been activated with a unique removable tip connected to the frame;
   (c) a number of times that communication has been initiated between the reader and the tag;
   (d) a number of times that data has been transmitted between the reader and the tag; and
   (e) a hash function wherein a unique value transmitted by the tag is analyzed to determine authenticity of the tag.

4. The device of claim 1, wherein the first and second antennas overlap at least partially when the tip is connected to the frame.

5. The device of claim 1, wherein the communication is carried out using an NFC protocol.

6. The device of claim 1, wherein the electromagnetic tag is a passive style tag.

7. The device of claim 1, wherein the first antenna projects into an interior space of the tip when the tip is connected to the frame.

8. The device of claim 1, wherein the second antenna is connected to an interior surface of the tip.

9. The device of claim 1, wherein the communication is carried out using the ISO/IEC 14443A protocol.

10. The device of claim 1, wherein the distal end of the tip includes at least two opposing sides forming a space therebetween, the space sized to admit application of a medical device into contact with the body tissue.

11. The device of claim 1, further including a light configured to shine in a direction of the distal end of the tip when the source of vibration is activated.

12. The device of claim 1, further including:
   a motor;
   a cam connected to the motor;
   a light source; and
   a light pipe connected to the light source to transmit light away from the light source, the light pipe connected to the cam to transmit vibration to a distal end of the tip.

13. The device of claim 1, further including:
   a battery;
   a coil connected to the battery, the coil configured to inductively receive electromagnetic energy to charge the battery.

14. The device of claim 1, wherein the electromagnetic tag includes an electronic component to store data that uniquely identifies the tag, the tag configured to transmit the stored data upon a read request from the electromagnetic reader.

15. The device of claim 14, wherein the component is configured to store data received from the electromagnetic reader.

16. The device of claim 15, wherein the data is at least one of:
   (a) a count of a number of times that the source of vibration has been activated with a unique removable tip connected to the frame;
   (b) an amount of time that the source of vibration has been activated with a unique removable tip connected to the frame;
   (c) a number of times that communication has been initiated between the reader and the tag;
   (d) a number of times that data has been transmitted between the reader and the tag; and
   (e) a unique value transmitted by the tag that is analyzable to determine authenticity of the tag.

17. The device of claim 1, wherein processing information includes preventing activation of the source of vibration if at least one of the following conditions are met:
   (a) a count of a number of times; or
   (b) an amount of time;
   that the source of vibration has been activated with a unique removable tip connected to the frame exceeds a predetermined threshold.

18. The device of claim 1, wherein the electromagnetic tag includes an electronic component to store data that includes a code useable to validate an authenticity of the tag.

19. The device of claim 1, wherein the removable tip includes a base connected to the distal end by a flexible sleeve affixed to both the base and the distal end, the device further including:
   a connector formed between the frame and the base, the connector requiring relative rotation between the base and the frame to connect and disconnect the removable tip;
   a coupling formed between the distal end and the frame to rotationally affix the distal end relative to the frame when the base is connected to the frame, whereby when the removable tip is rotated to be disconnected from the frame, the distal end is rotationally affixed relative to the base by the coupling to thereby cause the flexible sleeve to be torn.

20. An endpiece for therapeutically vibrating body tissue, the endpiece connectable to a frame having an activatable source of vibration and an electromagnetic reader and reader antenna, the endpiece comprising:
   a removable tip releasably connectable to the frame and having a distal end, the tip connected to the source of vibration when the tip is connected to the frame to thereby vibrate the distal end when the source of vibration is activated, the tip having an opening into which the reader antenna is inserted; and
   an electromagnetic tag connected to the removable tip and including a tag antenna configured to receive and send electromagnetic radiation using an NFC protocol in communication with the reader antenna, the tip and reader antennas disposed in proximity to each other when the removable tip is connected to the frame, the electromagnetic tag thereby configured to transmit information to the electromagnetic reader;
   the tag including data storage including a unique value transmittable by the tag to the reader that is analyzable to determine authenticity of the tag.

21. A method of vibrating body tissue, comprising:
   connecting a removable tip to a handheld frame, the tip having a distal end, the tip connected to a source of vibration when the tip is connected to the frame to thereby vibrate the distal end when the source of vibration is activated; and activating an electromagnetic reader within the frame and including a first antenna configured to send and receive electromagnetic radiation using an NFC protocol to read an electromagnetic tag connected to the removable tip and including a second antenna configured to receive and send electromagnetic radiation in communication with the electromagnetic reader antenna, the first antenna projecting into the removable tip, the first and second antennas thereby disposed proximate to each other when the removable tip is connected to the frame, the electromagnetic tag thereby configured to transmit information to the electromagnetic reader.

* * * * *